(12) United States Patent
Innes et al.

(10) Patent No.: US 6,995,253 B1
(45) Date of Patent: Feb. 7, 2006

(54) GENES FOR REGULATING DISEASE RESISTANCE IN PLANTS

(75) Inventors: Roger W. Innes, Bloomington, IN (US); Catherine A. Frye, Bloomington, IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/979,195

(22) PCT Filed: May 26, 2000

(86) PCT No.: PCT/US00/14718

§ 371 (c)(1),
(2), (4) Date: Apr. 2, 2002

(87) PCT Pub. No.: WO00/71696

PCT Pub. Date: Nov. 30, 2000

Related U.S. Application Data

(60) Provisional application No. 60/135,895, filed on May 26, 1999.

(51) Int. Cl.
*C12N 15/09* (2006.01)
*C12N 15/29* (2006.01)
*A01H 5/00* (2006.01)

(52) U.S. Cl. .................................. 536/23.6; 435/320.1
(58) Field of Classification Search ................ 800/279, 800/278, 306; 536/23.6; 435/320.1; 546/23.6
See application file for complete search history.

(56) References Cited

U.S. PATENT DOCUMENTS

| 5,792,904 A | 8/1998 | Ryals et al. | 800/200 |
| 6,057,490 A | 5/2000 | Ryals et al. | 800/265 |

FOREIGN PATENT DOCUMENTS

| WO | WO 98/04586 | 2/1998 |
| WO | WO 98/53073 | * 11/1998 |

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
Aist, J.R. et al., "Evidence that molecular components of papillae may be involved in ml-o resistance to barley powdery mildew", *Physiol. Molec. Plant Pathol*, 1988, 33, 17-32.
Baumann, E. et al., "Successful PCR-based reverse genetic screens using an En-1-mutagenised *Arabidopsis thaliana* population generated via single-seed descent", *Theor Appl. Genet.*, 1998, 97, 729-734.
Bird, C.R. et al., "Manipulation of plant gene expression by antisense RNA", *Biotechnology and Genetic Engineering Reviews*, 1991, 9, 207-227.
Boyd, L.A. et al., "The effects of allelic variation at the Mla resistance locus in barley on the early development of *Erysiphe graminis* f.sp. hordei and host responses", *Plant J.*, 1995, 7, 959-968.
Buschges, R. et al., "The barley Mlo Gene: A novel control element of plant pathogen resistance", *Cell*, 1997, 88, 695-705.
Cao, H. et al., "Characterization of an *arabidopsis* mutant that is nonresponsive to inducers of systemic acquired resistance", *The Plant Cell*, 1994, 6, 1583-1592.
Clark, K.L. et al., "Association of the *Arabidopsis* CTR1 Raf-like kinase with the ETR1 and ERS ethylene receptors", *PNAS*, 1998, 95, 5401-5406.
Frye, et al., "An *arabidopsis* mutant with enhanced resistance to powdery mildew", *The Plant Cell*, 1998, 10, 947-956.
Glazebrook, J. et al., "Isolation of *arabidopsis* mutants with enhanced disease susceptibility by direct screening", *Genetics*, 1996, 143, 973-982.
Hanks, S.K. et al., "The protein kinase family:Conserved features and deduced phylogeny of the catalytic domains", *Science*, 1988, 241, 42-52.
Hyde and Colhoun, "Mechanisms of resistance of wheat", *Phytopath. Z.*, 1975, 82, 185-206.
Jorgensen, J.H. "Discovery, characterization and exploitation of Mlo powdery mildew resistance in barley", *Euphytica*, 1992, 63, 141-152.
Kieber, J.J. "The ethylene response pathway in *arabidopsis*", *Annu. Rev. Plant. Physiol. Plant Mol. Biol.*, 1997, 48, 277-296.
Kolch, W. et al., "Raf-1 protein kinase is required for growth of induced NIH/3T3 cells", *Nature*, 1991, 349, 426-428.
Lagercrantz, U. et al., "Comparative mapping in *Arabidopsis* and *Brassica*, fine scale genome collinearity and congruence of genes controlling flowering time", *Plant J.*, 1996, 9, 13-20.
Ligternk, et al., "Receptor-mediated activation of a MAP kinase in pathogen defense of plants", *Science*, 1997, 276, 2054-2057.
Peterhansel, C. et al., "Interaction analyses of genes required for resistance responses to powdery mildew in barley reveal distinct pathways leading to leaf cell death", *Plant Cell*, 1997, 9, 1397-1409.

(Continued)

Primary Examiner—Medina A. Ibrahim
(74) Attorney, Agent, or Firm—Barnes & Thornburg LLP

(57) ABSTRACT

Provided in the present invention are isolated nucleotide sequences encoding EDR1 proteins, the disruption of which is associated with enhanced disease resistance in plants. The invention also provides vectors comprising said nucleotide sequences.

6 Claims, 6 Drawing Sheets

OTHER PUBLICATIONS

Pieterse, C.M. et al., "Systemic resistance in *arabidopsis* induced by biocontrol bacteria is independant of salicylic acid accumulation and pathogenesis-related gene expression", *Plant Cell*, 1996, 8, 1225-1237.

Radke, K. et al., "Characterization of maternal and zygotic D-raf proteins: Dominant negative effects on torso signal transduction", *Genetics*, 1997, 145, 163-171.

Uknes, S. et al., "Acquired resistance in *arabidopsis*", *Plant Cell*, 1992, 4, 645-656.

Waterhouse, P.M. et al, "Virus resistance and gene silencing in plants can be induced by simultaneous expression of sense and antisense RNA", *PNAS*, 1998, 95, 13959-13964.

Wolter, M. et al., "The mlo resistance alleles to powdery mildew infection in barley trigger a developmentally controlled defence mimic phenotype", *Mol. Gen. Genet*, 1993, 239, 122-128.

* cited by examiner

Figure 2

```
  1 ..................................MKHIFKKLHRGGNQ  14 SEQ ID NO: 2
                                        . :       | .
 51 KAKAERGGFDWDPSGGGGGDHRLNNQPNRVGNNMYASSLGLQRQSSGSSF 100 SEQ ID NO: 3

15 EQQNRTNDAAPPSDQNRIHVSANPPQAT..PSSVTETLPVAGATSSM...  59 SEQ ID NO: 2
    : . . |   |.   :  .|| :.    |       |     |
101 GESSLSGDYYMPT....LSAAANEIESVGFPQDDGFRLGFGGGGGDLRIQ 146 SEQ ID NO: 3

60 ..ASPAPTAASNRADYMSSEEEYQVQLALAISASNSQSSEDPEKHQIRAA 107 SEQ ID NO: 2
       |   | ..| :.   .|| ||·|||||:  |.  . |
147 MAADSAGGSSSGKSWAQQTEESYQLQLALALRLSSEATCADDPNFLDPVP 196 SEQ ID NO: 3

108 TLLSLGSHQRMDSRRDSSEVVAQRLSRQYWEYGVLDYEEKVVDSFY.... 153 SEQ ID NO: 2
         :|   .|    |: .| .:|  | | | :|| | ||
197 D.........ESALRTSPSSAETVSHRFWVNGCLSYYDKVPDGFYMMNG  236 SEQ ID NO: 3

154 ...DVYSLSTDSAKQGEMPSLEDLES..NHGTPGFEAVVVNRPIDSSLHE 198 SEQ ID NO: 2
    ::.|   |  .  | .||:| |  .    ||::|.|   |  .  |
237 LDPYIWTLCIDLHESGRIPSIESLRAVDSGVDSSLEAIIVDRRSDPAFKE 286 SEQ ID NO: 3

199 LLEIAECIALGCSTTSVSVLVQRLAELVTEHMGGSAEDSSIVLARWTEKS 248 SEQ ID NO: 2
    |     |.  |  ||   .|  .||.|:    |||            |  ..
287 LHNRVHDISCSCITT..KEVVDQLAKLICNRMGGPVIMGEDELVPMWKEC 334 SEQ ID NO: 3

249 SEFKAALNTCVFPIGFVKIGISRHRALLFKVLADSVRLPCRLVKGSHYTG 298 SEQ ID NO: 2
    :    :  | ||| . :|: |||||||||||| :  ||||: ||   |
335 IDGLKEIFKVVVPIGSLSVGLCRHRALLFKVLADIIDLPCRIAKGCKYCN 384 SEQ ID NO: 3

299 NEDDAVNTIRLEDEREYLVDLMTDPGTLIPADFASASNNTVEPCNSNGNK 348 SEQ ID NO: 2
    :| |   :|  :|||||||·  || |   |
385 RDDAASCLVRFGLDREYLVDLVGKPGHLWEPD.................  416 SEQ ID NO: 3

349 FPTAQFSNDVPKLSEGEGSSHSSMANYSSSLDRRTEAERTDSSYPKVGPL 398 SEQ ID NO: 2
                         |:|  ||:   .              ||
417 ..................SLLNGPSSISISS..............PL   431 SEQ ID NO: 3

399 RNIDYSSPSSVTSSTQLENNSSTAIGKGSRGAIIECSRTNMNIVPYNQNS 448 SEQ ID NO: 2
    |  :  |  | .
432 R...FPRPKPVEPAVDFRLLA............................ 449 SEQ ID NO: 3

449 EEDPKNLFADLNPFQNKGADKLYMPTKSGLNNVDDFHQQKNNPLVGRSPA 498 SEQ ID NO: 2
       |  |.|   .. . .:  |     :      ||·|  .||
450 ....KQYFSD.....SQSLNLVFDPASDDM.GFSMFHRQYDNP.......  482 SEQ ID NO: 3
```

Figure 2, cont.

```
499 PMMWKNYSCNEAPKRKENSYIENLLPKLHRDPRYGNTQSSYATSSSNGAI 548 SEQ ID NO: 2
                                                 | |:
483 ..............................................GGENDAL 489 SEQ ID NO: 3

549 SSNVHGRDNVTFVSPVAVPSSFTSTENQFRPSIVEDMNRNTNNELDLQPH 598 SEQ ID NO: 2
    . | |           ||.   :| | |           |::: |
490 AENGGGS........LPPSANMPPQNMMRAS..........NQIEAAPM 520 SEQ ID NO: 3

599 TAAVVHGQQNDESHIHDHRKYTSDDISTGCDPRLKDHESTSSSLDSTSYR 648 SEQ ID NO: 2
    |  :                                   |   .
521 NAPPI........................................SQPVPNRA 533 SEQ ID NO: 3

649 NDPQVLDDADVGECEIPWNDLVIAERIGLGSYGEVYHADWHGTEVAVKKF 698 SEQ ID NO: 2
    |  || |.  :||| || | |:|| ||:| |: |:|||.:||||
534 NRELGLDGDDM...DIPWCDLNIKEKIGAGSFGTVHRAEWHGSDVAVKIL 580 SEQ ID NO: 3

699 LDQDFSGAALAEFRSEVRIMRRLRHPNVVFFLGAVTRPPNLSIVTEFLPR 748 SEQ ID NO: 2
    ::|||    .||  || ||:|||||:| |:||||.||||||||:| |
581 MEQDFHAERVNEFLREVAIMKRLRHPNIVLFMGAVTQPPNLSIVTEYLSR 630 SEQ ID NO: 3

749 GSLYRILHR..PKSHIDERRRIKMALDVAMGMNCLHTSTPTIVHRDLKTP 796 SEQ ID NO: 2
    |||||:||:   :|||||: || ||| ||| ||   | |||||||.|
631 GSLYRLLHKSGAREQLDERRRLSMAYDVAKGMNYLHNRNPPIVHRDLKSP 680 SEQ ID NO: 3

797 NLLVDNNWNVKVGDFGLSRLKHNTFLSSKSTAGTPEWMAPEVLRNEPSNE 846 SEQ ID NO: 2
    |||||  : ||| |||||||| .||||||| ||||||||||||.|||||
681 NLLVDKKYTVKVCDFGLSRLKASTFLSSKSAAGTPEWMAPEVLRDEPSNE 730 SEQ ID NO: 3

847 KCDVYSFGVILWELATLRLPWRGMNPMQVVGAVGFQNRRLEIPKELDPVV 89 SEQ ID NO: 2
    | |||||||||||||||.  ||  :|| ||| ||||. :|||||: |.| |
731 KSDVYSFGVILWELATLQQPWGNLNPAQVVAAVGFKCKRLEIPRNLNPQV 78 SEQ ID NO: 3

897 GRIILECWQTDPNLRPSFAQLTEVLKPLNRLVLPTPQ.... 933 SEQ ID NO: 2
    ||  ||  :|  ||||| : :.|:|| :   .| |
781 AAIIEGCWTNEPWKRPSFATIMDLLRPLIKSAVPPPNRSDL 821 SEQ ID NO: 3
```

Figure 3

```
  1 MKHIFKKLHRGGNQEQQNRTNDAAPPS................DQNRIHV  34 SEQ ID NO: 2
    ||||||||||       |. . |       .      . | :
  1 MKHIFKKLHHSNRSNDAQSTSSISSSSSPASSLSSASCTTDHRNSNSVSQ  50 SEQ ID NO: 4

35 SANPPQATPSSVTETLPVA..GATSSMASPAPTAASNRADYMSSEEEYQV  82 SEQ ID NO: 2
    |  |  .. ||||  ||       . .. ||.|||||||
 51 SPLSPSTISTASTTTTPAAPVGAGGGGGGGNLSTINRQQDYYTSEEEYQV 100 SEQ ID NO: 4

83 QLALAISASNSQSSEDPEKHQIRAATLLSLGSHQRMDSRRDSSEVVAQRL 132 SEQ ID NO: 2
    |||||:| |.|| |:||    :  ..    .|    .|  ||  ': ||
101 QLALALSVSSSQ.SQDPFPSDVNSSNGHGVG.RTAVDLARDREDAAADLL 148 SEQ ID NO: 4

133 SRQYWEYGVLDYEEKVVDSFYDVYSLSTDSAKQGEMPSLEDLESNHGTPG 182 SEQ ID NO: 2
    |||||:|||:||||||||| |||||.| || |  .|.|||| :||.| ||
149 SRQYWDYGVMDYEEKVVDGFYDVYNLFTDPASRGKMPSLSELETNPGTSN 198 SEQ ID NO: 4

183 FEAVVVNRPIDSSLHELLEIAECIALGCSTTSVSVLVQRLAELVTEHMGG 232 SEQ ID NO: 2
    || |::|. || || ||::|| || |  | :|.|| ||.|||| |:||
199 FEGVIINQRIDPSLEELMQIAHCITLDCPASEISLLVLRLSELVTGHLGG 248 SEQ ID NO: 4

233 SAEDSSIVLARWTEKSSEFKAALNTCVFPIGFVKIGISRHRALLFKVLAD 282 SEQ ID NO: 2
    .|..|:||:| |  |.| : .|.| | ||| .|||:||||||||||||||
249 PVKDANIILAKWMEISTELRTSLHTSVLPIGSLKIGLSRHRALLFKVLAD 298 SEQ ID NO: 4

283 SVRLPCRLVKGSHYTGNEDDAVNTIRLEDEREYLVDLMTDPGTLIPADFA 332 SEQ ID NO: 2
    | :|||||||||||| ||||||   ::|  .: |:|||||   |||||||
299 HVGIPCRLVKGSHYTGVEDDAVNIVKLPNDSEFLVDLMGAPGTLIPADVL 348 SEQ ID NO: 4

333 SASNNTVEPCNSNGNKFPTAQFSNDVPKLSEGEGSSHSSMANYSSSLDRR 382 SEQ ID NO: 2
    ||  .      |    .|      |.|.    |   :
349 SAKDASFNSPKLNKIPSLPSNSHSGVSYPRRNLLSGQNSVLGDDFSGRSK 398 SEQ ID NO: 4

383 TEAERTDSSYPKVGPLRNIDYSSPSSVTSSTQLENNSSTAIG.....KGSR 428 SEQ ID NO: 2
    |  . |  |    |   . *|| |.:  |  |||    ||  |
399 PEKIESVHSISDAGGSSTAGSSGINKRPSSNQVDWTSPLAIGTSLYKGGR 448 SEQ ID NO: 4

429 G..AIIECSRTNMNIVPYNQNSEEDPKNLFADLNPFQNKGADKLYMPTKS 476 SEQ ID NO: 2
    |  |  : | |.|:|||.||. ||||||||||||||||||| ||.   :
449 GPNAAGDGLRLNVNVVPYDQNNPEDPKNLFADLNPFQIKGSGNTLLQKNP 498 SEQ ID NO: 4

477 GLNNVDDFHQQKNNPLVGRSPAPMMWKN.YSCNEAPKRKENSYIENLLPK 525 SEQ ID NO: 2
    | | :  |   : || |||||||| |. || || |  | |||
499 ARNKVSELQQPINTLIPGRPPAPMMWKNRYAPNEVP.RKNESDSEGLFPK 547 SEQ ID NO: 4
```

Figure 3, cont.

```
526 LHRDPRYGNTQSSYATSSS....NGAISSNVHGRDNVTF.....VSPVAV 566 SEQ ID NO: 2
        . | | .|||.    .| .||    :       |.
548 KNGGSSGYNISSIASTSSNIPQKSSTDTSRLHGNSRPAYRGNDEVASTRN 597 SEQ ID NO: 4

567 PSSFTSTENQFRPSIVEDMNRNTNNELDLQPHTAAVVHGQQ....NDESH 612 SEQ ID NO: 2
    || | | :||    |:.   |     : |.    .    |:
598 NSSILSAELEFRRLSVQNSQNNNRETSQWEGHSLQSDDLNRTQAYGDDII 647 SEQ ID NO: 4

613 IHDHRKYTSDDISTGCDPRLKDHESTSSSLDSTSYRNDPQVLDDADVGEC 662 SEQ ID NO: 2
    :         | | . :||: |. .|| .   . || | | |||:|
648 VESDHTRNLQAQSIGTNIKLKEPENPTSSGNLGPSQVDP.VFD..DVGDC 694 SEQ ID NO: 4

663 EIPWNDLVIAERIGLGSYGEVYHADWHGTEVAVKKFLDQDFSGAALAEFR 712 SEQ ID NO: 2
    |||| ||||  |||||||||||||||||.|||||||||||||||||||:
695 EIPWEDLVIGERIGLGSYGEVYHADWNGTEVAVKKFLDQDFSGAALAEFK 744 SEQ ID NO: 4

713 SEVRIMRRLRHPNVVFFLGAVTRPPNLSIVTEFLPRGSLYRILHRPKSHI 762 SEQ ID NO: 2
    ||||||||.|||||  |:||:||||.|||:|||||||||||||:|||  |
745 REVRIMRRLRHPNVVRFMGAITRPPHLSIITEFLPRGSLYRIIHRPHFQI 794 SEQ ID NO: 4

763 DERRRIKMALDVAMGMNCLHTSTPTIVHRDLKTPNLLVDNNWNVKVGDFG 812 SEQ ID NO: 2
    |||.:|||||||| ||.||||| |||||||||||.||||| .||||| |||
795 DERQKIKMALDVAKGMDCLHTSNPTIVHRDLKSPNLLVDTDWNVKVCDFG 844 SEQ ID NO: 4

813 LSRLKHNTFLSSKSTAGTPEWMAPEVLRNEPSNEKCDVYSFGVILWELAT 862 SEQ ID NO: 2
    |||||||||||||||||||||||||||||||||||||:|||||||||||
845 LSRLKHNTFLSSKSTAGTPEWMAPEVLRNEPSNEKCDIYSFGVILWELAT 894 SEQ ID NO: 4

863 LRLPWRGMNPMQVVGAVGFQNRRLEIPKELDPVVGRIILECWQTDPNLRP 912 SEQ ID NO: 2
    ||||| |||||||||||||||||:||||||||:| ||| |||||||||||
895 LRLPWSGMNPMQVVGAVGFQNKRLEIPKELDPIVARIIWECWQTDPNLRP 944 SEQ ID NO: 4

913 SFAQLTEVLKPLNRLVLPTPQ................ 933 SEQ ID NO: 2
    |||||| | || |||:|
945 SFAQLTVALTPLQRLVIPAYVDQLNSRLPQEISVNSTP 982 SEQ ID NO: 4
```

Figure 4

GENES FOR REGULATING DISEASE RESISTANCE IN PLANTS

This application claims priority to U.S. Provisional Application No. 60/135,895, filed May 26, 1999, the entirety of which is incorporated by reference herein.

Pursuant to 35 U.S.C. §202(c), it is acknowledged that the U.S. Government has certain rights in the invention described herein, which was made in part with funds from the National Institutes of Health, Grant No. GM46451.

FIELD OF THE INVENTION

This invention relates to the field of plant pathology and disease resistance. In particular, this invention relates to a novel gene and protein involved in the resistance of plants to various microbial pathogens.

BACKGROUND OF THE INVENTION

Various scientific and scholarly articles are referred to throughout the specification. These articles are incorporated by reference herein to describe the state of the art to which this invention pertains.

Plants defend themselves against pathogens through both pre-formed and inducible resistance mechanisms. Among the inducible responses are the hypersensitive resistance (HR) response and systemic acquired resistance (SAR). The HR is a localized plant response characterized by a suite of physiological changes culminating in plant cell death and cessation of pathogen growth. SAR is a systemic resistance response that is induced after formation of a necrotic lesion, either as part of the HR or as a symptom of disease. Although the HR and SAR have been the major forms of induced plant resistance studied, evidence for other resistance mechanisms exists.

The HR can be induced by the interaction between a plant resistance gene and a matching pathogen avirulence gene. Such "gene-for-gene" interactions provide a narrow range of resistance as they differentiate between races of a pathogen based on expression of a specific avirulence gene. Resistance gene products are thought to function as receptors for ligands produced directly or indirectly by avirulence genes. Multiple biochemical events are associated with the HR, including an oxidative burst, K/Cl ion exchange, deposition of autofluorescent compounds and callose in the cell wall, synthesis of antimicrobial phytoalexins, and cell death.

In *Arabidopsis*, SAR is associated with the expression of three pathogenesis-related genes: PR-1 (unknown function), BGL2 (β-glucanase, also known as PR-2) and PR-5 (a thaumatin-like protein). *Arabidopsis* mutants identified based upon constitutive expression of PR genes (cpr1 and cpr5) are resistant to the fungal pathogen *Peronospora parasitica* and the bacterial pathogen *Pseudomonas syringae* pv maculicola. Other mutants that constitutively express PR genes have been isolated based upon the development of spontaneous leaf lesions that are similar in appearance to the lesions of an HR. These lesion mimic mutants also show resistance to both fungal and bacterial pathogens.

Methyl jasmonate and ethylene may induce a defense pathway that is independent of SA. Wounding as well as pathogen attack induce the production of jasmonic acid, which in turn induces defense genes other than those associated with SAR, including genes that encode defensins and thionins. Defensins and thionins are low molecular weight polypeptides that have potent antimicrobial activity in vitro. *Arabidopsis* plants over-expressing endogenous thionin have increased resistance to the fungal pathogen *Fusarium oxysporum*. Transgenic *Arabidopsis* plants unable to accumulate SA and thus unable to express SAR are able to respond to the jasmonic acid signal and express both defensin and thionin genes. Mutants that constitutively express the proposed jasmonic acid pathway, but not the SA pathway have not been reported; however, the cpr5 and acd2 mutants of *Arabidopsis* constitutively expresses both PR genes and defensin.

Another defense pathway that is independent of SA is induced by the biocontrol bacterium *P. fluorescens* and is termed induced systemic resistance (ISR) (Pieterse, et al., 1996, Plant Cell 8:1225–1237). ISR is observed when *Arabidopsis* plants grown in soil containing *P. fluorescens* are challenged with virulent bacterial and fungal pathogens. Under these conditions, the *Arabidopsis* plants develop less severe disease symptoms than do control plants grown in soil alone. ISR is not associated with the expression of PR genes and is observed in plants unable to accumulate SA, indicating that this pathway is independent of SAR (Pieterse, et al., 1996, supra). It has not been determined whether the proposed jasmonic acid pathway contributes to ISR.

Screens for plant mutants that display enhanced resistance to virulent pathogens have been performed with several crop species. From these studies, barley resistant to powdery mildew (the mlo mutation), sugar-cane resistant to smut, mulberry resistant or tolerant to nematodes, mulberry resistant to Dogare disease and peppermint resistant to *Verticillium* wilt were identified. Of these, only the mlo resistance has been well characterized.

The mlo mutation of barley mediates resistance to all common races of the powdery mildew fungus *Erysiphe graminis* f sp *hordei* and, thus, provides a broader spectrum resistance than do the gene-for-gene type of resistance genes (Jorgensen, 1992, Euphytica 63:141–152).

Resistance in mlo mutants correlates with the formation of cell wall appositions that may prevent fungal penetration (Jorgensen, 1992, supra; Wolter et al., 1993, Mol. Gen. Genet. 239:122–128) and with plant cell death (Peterhänsel et al., 1997, Plant Cell 9:1397–1409). Defense genes are not constitutively expressed in mlo mutant barley; however, they are induced more rapidly upon infection by *E. graminis* (Peterhänsel, et al., 1997, supra). The wild-type Mlo gene has been cloned and is hypothesized to be a negative regulator of defense responses such that mutant mlo alleles mediate resistance by allowing abnormal defense responses to occur both spontaneously and during an *E. g. hordei* infection (Wolter, et al., 1993, supra; Buschges et al., 1997, Cell 88:695–705).

The isolation of novel mutants and genes that control defense responses will broaden the range of affected pathogens. It would be particularly advantageous to isolate mutants or genes involved in inducibly enhanced disease resistance without spontaneously occurring abnormal defense responses. Novel regulatory mutants are likely to have distinct pathogen ranges due to differential induction of unique subsets of genes. The different enhanced response may yield resistance responses that are spatially distinct (i.e. epidermal v. mesophyll cells), temporally distinct (i.e. affecting early v. late stages of infection), and/or comprised of a distinct subset of defense mechanisms (i.e. formation of necrotic lesions, deposition of callose, synthesis of antimicrobial Phytoalexins and others). The isolation of mutants will yield the critical gene(s), which can be used to transgenically transfer the enhanced resistance trait to new species.

SUMMARY OF THE INVENTION

Provided in the present invention is a novel gene (referred herein as EDR1), the disruption of which is associated with enhanced disease resistance in plants. The invention further provides transgenic plants and mutants having an enhanced resistance to plant pathogens. In these plants disease resistance is enhanced in a manner that does not involve constitutive expression of pathogenesis-related (PR) genes.

According to one aspect of the present invention, a disease resistance gene, EDR1, is provided. The EDR1 gene is located on *Arabidopsis thaliana* chromosome 1 between the ATEAT and NCC1 markers. The disruption of the EDR1 gene is associated with enhanced resistance to plant pathogens or other disease-causing agents. In a preferred embodiment, this gene encodes a protein with a kinase domain. In a more preferred embodiment, the gene contains exons that encode a protein that is 900–1000 amino acids in length. In a yet more preferred embodiment, the nucleic acid molecule contains an open reading frame that encodes a protein that is at least 50% identical over its full length to SEQ ID NO:2, and in a particularly preferred embodiment encodes SEQ ID NO:2. In a more particularly preferred embodiment, the nucleic acid molecule is comprised of SEQ ID NO:1.

Provided with this aspect of the invention is a cDNA molecule comprising the exons of the gene which encode a polypeptide 900–1000 amino acids in length. Also provided with this aspect of the invention is a nucleic acid molecule of at least 15 nucleotides in length, preferably at least 20 nucleotides in length, and most preferably at least 27 nucleotides in length, that is identical in sequence to a portion of the EDR1 gene located on *Arabidopsis thaliana* chromosome 1. In a preferred embodiment, the invention provides a nucleic acid molecule of at least 15, preferably 20, and most preferably 27 nucleotides in length, that is identical to or complementary to a consecutive 15, 20 or 27 nucleotide portion, respectively, of the sequence set out in SEQ ID NO:1.

According to another aspect of the invention an isolated nucleic acid is provided that is a plant gene and whose disruption is associated with enhanced resistance to plant pathogens or other disease-causing agents. This nucleic acid has a sequence that is selected from SEQ ID NOS:1, 5 or 9, a nucleic acid sequence that is at least 60% identical to SEQ ID NOS:1, 5 or 9 a nucleic acid encoding any of SEQ ID NOS:2, 4, 6 or 10, and a nucleic acid encoding a sequence that is at least 50% identical to any of SEQ ID NOS:2, 4, 6 or 10. Provided with this aspect of the invention is a polypeptide that is produced by the expression of the isolated nucleic acid molecule, and antibodies immunologically specific for the polypeptide. Also provided with this aspect of the invention is a nucleic acid molecule of, preferably, at least 27 nucleotides in length, more preferably, at least 20 nucleotides in length and, most preferably, 15 nucleotides in length that is identical in sequence to a consecutive 27, 20 or 15 base pair portion, respectively, of the sequence of the isolated nucleic acid molecule set forth above.

According to another aspect of the invention, a method is provided to enhance resistance of a plant to plant pathogens or other disease agents. This method comprises the removal of the EDR1 function from the plant cell. In a preferred embodiment, the removal of EDR1 function is accomplished by the addition of transgenes. The transgene preferably is comprised of at least 15 nucleotides of the gene on chromosome 1 of *Arabidopsis thaliana*. In a particularly preferred embodiment, the transgene expresses a mutant version of the EDR1 protein that interferes with the function of the native version of the protein (i.e., a "dominant negative" form). In a more particularly preferred embodiment, the nucleic acid is mutated in the portion encoding the kinase domain of EDR1. In a most preferred embodiment, the nucleic acid molecule is SEQ ID NO:1 and the coding sequence for residue 696 is mutated. In another more preferred embodiment, the transgene is comprised of at least 15 nucleotides of SEQ ID NO:1, sequences encoding SEQ ID NO:2, SEQ ID NO:4, SEQ ID NO:6 or SEQ ID NO:7, or variants thereof. In a preferred embodiment, the transgene expresses the antisense strand of the nucleic acid molecule encoding EDR1. In another preferred embodiment, the transgene expresses the sense strand of the nucleic acid molecule. In a particularly preferred embodiment, transgenes express both the sense and anti-sense strands of the nucleic acid molecule. This aspect of the invention also provides a plant made from this method, and a reproductive unit from the plant, e.g., a seed. In a most preferred embodiment, the plant is *Arabidopsis thaliana*.

According to another aspect of the invention, a method is provided for screening plants for mutations conferring enhanced disease resistance by pathways that do not involve constitutive PR gene expression. The method comprises the following basic steps: (a) provide a plant variety and a pathogen to which the plant normally is not resistant; (b) inoculate a population of the plant variety with the pathogen; (c) select a sub-population of the plants that exhibit a disease-resistance response; and (d) eliminate from the sub-population any plants exhibiting constitutive PR gene expression.

The above method can be modified or optimized in a variety of ways, including, but not limited to: (1) using *Arabidopsis* as the plant for screening; most preferably using variety Col—O and the pathogen *Pseudomonas syringae*, to which Col—O is sensitive; (2) optionally, treating the plants (seeds) with a mutagenizing agent (such as fast-neutron bombardment, exposure to ethyl methanesulfonate, or exposure to gamma irradiation) prior to inoculation with the pathogen; (3) in the sub-population of plants exhibiting a disease resistance response, eliminating individuals exhibiting a hypersensitive response (HR); and (4) challenging the selected resistant plants to other plant pathogens to further select for broad spectrum resistance. In the last instance, it is particularly preferred to determine whether the selected resistant plants are resistant to several classes of plant pathogens. Accordingly, if the initial pathogen used in the screen was a bacterium, for example, the secondary screen might be against a fungal or viral pathogen.

According to another aspect of the invention, mutant *Arabidopsis* plants produced by the above-described method are provided. In preferred embodiments, mutants edr1, edr2, edr3 and edr4 are provided. These mutants each comprise mutations in different genes, the mutations resulting in the plants' enhanced disease resistance. In another preferred embodiment, the wild-type genes, EDR1 (described in greater detail below), EDR2, EDR3 and EDR4, corresponding to the mutated genes in the aforementioned edr1, edr2, edr3 and edr4 *Arabidopsis* mutants, respectively, are also provided.

Other features and advantages of the present invention will be better understood by reference to the drawings, detailed description and examples that follow.

BRIEF DESCRIPTION OF THE DRAWINGS

FIG. 1. Response of edr1 plants to *P. syringae*. *Arabidopsis* plants were vacuum infiltrated with *P. syringae* and bacterial growth in plant leaves monitored over 4 days. Data points represent the mean±SE of three samples. Each graph is representative of at least three experiments.

FIG. 2. Alignment of the *Arabidopsis* EDR1 and CTR1 proteins. SEQ ID NO: 2, representing EDR1 amino acid sequence, and SEQ ID NO: 3, representing CTR1 amino acid sequence were aligned using the GCG GAP program with a gap creation penalty of 12 and a gap extension penalty of 2. Vertical bars indicate amino acid identities, dots indicate functionally similar amino acids. The highly similar region from residue 668 to the end of SEQ ID NO: 2 (residue 933) corresponds to the kinase domain.

FIG. 3. Alignment of *Arabidopsis* EDR1 and tomato TCTR2 predicted amino acid sequences. SEQ ID NO: 2 represents EDR1 amino acid sequence, and SEQ ID NO: 4 represents TCTR2 amino acid sequence.

FIG. 4. Alignment of the kinase domains of the *Arabidopsis* EDR1 (SEQ ID NO: 2), TCTR2 (SEQ ID NO: 4), Rice EDR1 (SEQ ID NO: 6), and a *Arabidopsis* CTR1 (SEQ ID NO: 3) proteins. Black boxes indicate identical amino acids. Arrows indicate regions that distinguish CTR1 from the other three genes. These regions can be used to develop PCR primers that will specifically amplify EDR1-homologous genes from both monocot and dicot species.

DETAILED DESCRIPTION OF THE INVENTION

I. Definitions

Figure 1A:
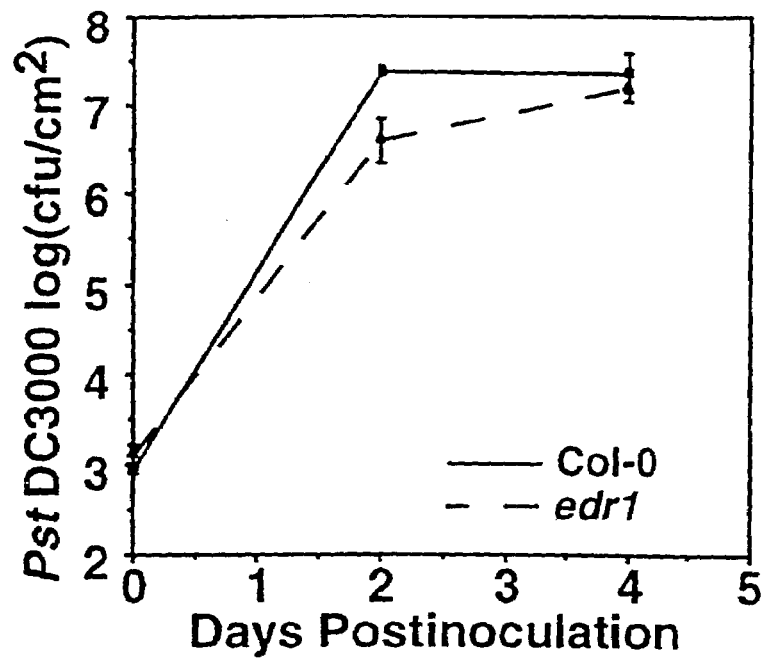
FIG. 1A. Time course of *P.s. tomato* DC3000 growth in *Arabidopsis* leaves.

Various terms relating to the biological molecules of the present invention are used hereinabove and also throughout the specifications and claims.

With respect to the genotypes of the invention, the terms "EDR1" and "edr1" are used. The term "EDR1" is used to designate the naturally-occurring or wild-type genotype. This genotype has the phenotype of naturally-occurring spectrum of disease resistance and susceptibility. The term "edr1" refers to a genotype having recessive mutation(s) in the wild-type EDR1 gene. The phenotype of edr1 individuals is enhanced disease resistance. Where used hereinabove and throughout the specifications and claims, the term "EDR1" refers to the protein product of the EDR1 gene.

In reference to the mutant plants of the invention, the term "null mutant" is used to designate an organism or genomic DNA sequence with a mutation that causes the product of the EDR1 gene to be non-functional or largely absent. Such mutations may occur in the coding and/or regulatory regions of the EDR1 gene, and may be changes of individual residues, or insertions or deletions of regions of nucleic acids. These mutations may also occur in the coding and/or regulatory regions of other genes which may regulate or control the EDR1 gene and/or the product of the EDR1 gene so as to cause said gene product to be non-functional or largely absent.

With reference to nucleic acids of the invention, the term "isolated nucleic acid" is sometimes used. This term, when applied to genomic DNA, refers to a DNA molecule that is separated from sequences with which it is immediately contiguous (in the 5' and 3' directions) in the naturally-occurring genome of the organism from which it was derived. For example, the "isolated nucleic acid" may comprise a DNA molecule inserted into a vector, such as a plasmid or virus vector, or integrated into the genomic DNA of a procaryote or eukaryote. An "isolated nucleic acid molecule" may also comprise a cDNA molecule or a synthetic DNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

Nucleic acid sequences and amino acid sequences can be compared using computer programs that align the similar sequences of the nucleic or amino acids thus define the differences. For purposes of this invention, the GAP program from the GCG Wisconsin Package Version 9.1 (available from the "Genetics Computer Group", Madison, Wis.) with a gap creation penalty of 12 and a gap extension penalty of 2 is used herein to compare sequence identity and similarity.

The term "substantially the same" refers to nucleic acid or amino acid sequences having sequence variations that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

With respect to antibodies of the invention, the terms "immunologically specific", "immunospecific" or "specific" refer to antibodies that bind to one or more epitopes of a protein of interest, but which do not substantially recognize and bind other molecules in a sample containing a mixed population of antigenic biological molecules.

With respect to oligonucleotides, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "promoter region" refers generally to the transcriptional regulatory regions of a gene, which may be found at the 5' or 3' side of the coding region, or within the coding region, or within introns.

The term "reporter gene" refers to genetic sequences which may be operably linked to a promoter region forming a transgene, such that expression of the reporter gene coding region is regulated by the promoter and expression of the transgene is readily assayed. The term "selectable marker gene" refers to a gene product which when expressed confers a selectable phenotype, such as antibiotic resistance, on a transformed cell or plant. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequences used to transform plants or other organisms (e.g., bacteria, yeast). When transforming plants, these constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 2000.

II. Description

In accordance with the present invention, a gene is provided that is a novel regulator of plant disease resistance. This gene, EDR1, was initially isolated from Arabidopsis thaliana. Its manner of regulating disease resistance is novel and surprising. When the functional product of the gene is eliminated, the plants exhibit enhanced disease resistance, but without infection the plants do not exhibit constitutive expression of the pathogenesis-related genes or spontaneous necrotic lesions. Additionally, the induction of the pathogenesis-related genes and the halting of pathogen growth occurs later after infection than observed with other inducible disease defense responses.

The EDR1 gene was first isolated in a mutated form (edr1) from libraries of mutagenized Arabidopsis seed. The edr1 mutant was isolated firstly because of its enhanced resistance to the pathogenic bacterium Pseudomonas syringae tomato DC3000. Secondly, the edr1 mutant was selected because it did not have constitutive expression of the PR-1 gene.

Additionally, the edr1 mutant was found to have reduced susceptibility to Pseudomonas syringae maculicola M4 and the powdery mildew fungus Erysiphe cichoracearum. The expression of the SAR-related genes, PR-1, PR-5 and BGL2, was not detectable prior to inoculation with E. cichoracearum, indicating that the edr1 mutant does not function by way of constitutive stimulation of the SAR pathway. Three days after infection, the PR-1 message was four times higher in the mutant than wildtype plants, indicating that the mutant displays stronger induction of the SAR pathway in response to normally virulent pathogens than does the wild-type plant.

The enhanced disease resistance of the edr1 mutant segregates as a recessive trait. Genetic linkage analysis establishes that the EDR1 gene is located on chromosome 1, 3.2 centiMorgans centromeric from the SSLP (simple sequence length polymorphism) marker ATEAT1 and 0.85 centiMorgans telomeric from the CAPS (co-dominant amplified polymorphic sequence) marker NCC1.

The EDR1 gene was isolated using a positional cloning approach. Two overlapping bacterial artificial chromosome (BAC) clones containing Arabidopsis genomic DNA were identified that contained closely-linked molecular markers. Sequence information from the Arabidopsis Genome Project was used to create additional molecular markers and allowed the EDR1 gene to be mapped to a 100 kb interval. Sequence analysis of this 100 kb region revealed 25 potential protein coding genes. Candidate genes were sequenced from the edr1 mutant and compared to the known wildtype sequence. Upon sequencing a gene with similarity to MAP3 kinases (also known as "mitogen activated protein kinase kinase kinase"), a single nucleotide difference was found that produces a premature stop codon, thereby truncating the C-terminal half of the protein containing the kinase domain. This null mutation fits well with the recessive nature of the edr1 mutation and this MAP3 kinase gene co-segregates with the EDR1 gene, therefore this MAP3 kinase gene is referred to as the EDR1 gene (a cDNA is SEQ ID NO:1 and the genomic clone is found on BAC F22O13, Genbank AC003981, and in Genbank at No. AAC14047.1). The EDR1 predicted protein (SEQ ID NO:2) is 933 amino acids long and contains a "kinase domain" from residues 668 to 933 (Hanks et al., 1988, Science 241:42–52).

Although the EDR1 genomic clone and cDNA from Arabidopsis thaliana are described and exemplified herein, this invention is intended to encompass nucleic acid sequences and proteins from other plants that are sufficiently similar to be used instead of the Arabidopsis EDR1 nucleic acid and proteins for the purposes described below. These include, but are not limited to, allelic variants and natural mutants of SEQ ID NO:1, which are likely to be found in different species of plants or varieties of Arabidopsis. Because such variants are expected to possess certain differences in nucleotide and amino acid sequence, this invention provides an isolated EDR1 nucleic acid molecule having at least about 50% (preferably 60%, more preferably 70% and even more preferably over 80%) sequence identity in the coding regions with the nucleotide sequence set forth as SEQ ID NO:1 (and, most preferably, specifically comprising the coding region of SEQ ID NO:1). This invention also provides isolated polypeptide products of SEQ ID NO:1, having at least about 50% (preferably 60%, 70%, 80% or greater) sequence identity with the amino acid sequences of SEQ ID NO:2. Because of the natural sequence variation likely to exist among EDR1 genes, one skilled in the art would expect to find up to about 30–40% nucleotide sequence variation, while still maintaining the unique properties of the EDR1 gene and encoded polypeptide of the present invention. Such an expectation is due in part to the degeneracy of the genetic code, as well as to the known evolutionary success of conservative amino acid sequence variations, which do not appreciably alter the nature of the encoded protein. Accordingly, such variants are considered substantially the same as one another and are included within the scope of the present invention.

Many diverse kinases are involved the signal transduction pathways; however, the kinase domain is highly conserved in all kinases. The EDR1 protein sequence contains regions of high similarity to a large number of protein kinases. The functional specialization that allows these kinases to operate in specific signal transduction pathways lies both in the kinase domain and non-kinase domains. The *Arabidopsis* CTR1 kinase protein (SEQ ID NO:3) displays moderate similarity to EDR1 (40% identity, 49% similarity). While the similarity is highest in the putative kinase domain (residues 668–933 of SEQ ID NO:2), it extends to the rest of the protein as well (FIG. 2) suggesting a possible similarity of specialization. CTR1 is a negative regulator of the ethylene response pathway (Kieber, 1997, Annu. Rev. Plant Physiol. Plant Mol. Biol. 48:277–296). By analogy, EDR1 may function as a negative regulator of specific defense response pathways.

EDR1 genes have been identified in crop plants by their extensive homology to EDR1 outside the kinase region. The tomato TCTR2 predicted protein sequence (SEQ ID NO:4) shows extensive homology throughout the protein sequence (55% identity, 61% similarity) (FIG. 3). TCTR2 is more similar to EDR1 than CTR1 is to EDR1, both inside and outside the kinase region (Table 1), but the high similarity outside the kinase region in particular indicates that they are homologous proteins.

EDR1 also shows a high similarity to a gene product from rice (SEQ ID NOS:5 and 6 for the cDNA and predicted amino acid sequences, respectively). The amino acid sequence encoded by this rice gene is 85% identical to EDR1 in the kinase domain. This high degree of identity is comparable to the TCTR2-EDR1 identity of 86% in the kinase region, indicating that the rice gene is also part of an EDR1 gene family.

TABLE 1

Comparison of amino acid sequences EDR1 to CTR1, TCTR2 and Rice EDR.

|  | CTR1 | TCTR2 | RICE EDR |
|---|---|---|---|
| Region I (1–667 aa) | | | |
| Identity | 25% | 43% | — |
| Similarity | 32% | 49% | — |
| Region II - Kinase (668–933 aa) | | | |
| Identity | 65% | 86% | 85% |
| Similarity | 74% | 90% | 88% |

An EDR1 homolog from barley also has been identified. A cDNA sequence corresponding to the barley EDR1 homolog and its predicted amino acid sequence are set forth herein as SEQ ID NO:9 and SEQ ID NO:10, respectively.

The present invention encompasses these EDR1 genes from tomato, rice and barley, as well as TCTR2. The isolation of four EDR1 genes enables the isolation of additional EDR1 genes. The known EDR1 genes encompass both monocots and dicots and therefore are excellent candidates for determining conserved amino acid sequences that can be used as probes to identify new EDR1 genes from the entire plant kingdom. The sequences on which to base such probes are indicated by arrows in FIG. 4, however many other sequences are present that would be equally as appropriate. The criteria for selecting probe sequence is that they should be well conserved among the EDR1 homologs EDR1, TCTR2 and the rice and barley EDR1, but not conserved in the general kinase CTR1, and therefore will only identify EDR1 homologous kinases. Indeed, the utility of this strategy was proven by the identification of the barley EDR1 gene, using two degenerate oligonucleotides corresponding to the amino acid sequences indicated by the arrows in FIG. 4 (SEQ ID NOS: 7 and 8). These primers were used to amplify the intervening region of EDR1 homologs from barley using cDNA as a template. The PCR products were then cloned and sequenced, revealing several identical clones that were over 90% identical to the rice EDR1 sequence. To obtain the full length cDNA sequence of this gene, 5' and 3' RACE ("rapid amplification of cDNA ends") PCR was performed.

The edr1 mutant from *Arabidopsis* is also part of the present invention. It exhibits an enhanced disease resistance with characteristics of regulation that have not been previously observed. This mutant is novel in its ability to poise the plant metabolism for a heightened disease-resistance response without the constitutive induction of the pathogenesis-related genes and non-infection related necrotic lesions on leaf tissue.

Furthermore, upon infection, the pathogenesis-related genes are induced much later than currently known disease resistance mutants, resulting in a halting of pathogen growth at a later stage of infection. This distinction is useful because the enhanced disease resistance pathways exhibited by edr1 mutants of this invention are not constitutive in the uninfected plant, and so do not cause death of tissue vital for photosynthesis until the plant is actually challenged with a pathogen. Additionally, the edr1 mutants may well be effective against a spectrum of diseases because they are active against a later infection stage. Due to the unique phenotype conferred by the edr1 mutation, it is easy to screen populations of mutagenized plants and obtain other edr1 mutants. Such edr1 mutants from all other species of plants are considered to be within the scope of this invention.

It is contemplated that the present invention encompasses not only other plant homologs of the EDR1 gene, but also using these homologs to engineer enhanced disease resistance in other plant species. The edr1 mutant establishes that null mutations in this gene result in plants with enhanced disease resistance. Once the EDR1 homolog of a specific species is isolated, established methods exist to create transgenic plants that are deficient in the EDR1 gene product. These edr1-like transgenic plants are also considered part of the invention.

The following sections set forth the general procedures involved in practicing the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (2000) (hereinafter "Ausubel et al.") are used.

III. Preparation of edr1 Mutants, EDR1 Nucleic Acids, Proteins, Antibodies and Transgenic Plants.

A. Isolation of EDR1 Genetic Mutants

Populations of plant mutants are available from which edr1 mutants in other plant species can be isolated. Many of these populations are very likely to contain plants with null mutations in the EDR1 gene. Such populations can be made by chemical mutagenesis, radiation mutagenesis, and transposon or T-DNA insertions. The methods to make mutant populations are well known in the art.

The nucleic acids of the invention can be used to isolate edr1 mutants in other species. In species such as maize where transposon insertion lines are available, oligonucleotide primers can be designed to screen lines for insertions in the EDR1 gene. Plants with transposon or T-DNA insertions in the EDR1 gene are very likely to have lost the function of the gene product. Through breeding, a plant line may then be developed that is homozygous for the non-functional copy of the EDR1 gene. The PCR primers for this purpose are designed so that a large portion of the coding sequence the EDR1 gene are specifically amplified using the sequence of the EDR1 gene from the species to be probed (see Baumann et al., 1998, Theor. Appl. Genet. 97:729–734).

Other edr1-like mutants can easily be isolated from mutant populations using the distinctive phenotype characterized in accordance with the present invention. This approach is particularly appropriate in plants with low ploidy numbers where the phenotype of a recessive mutation is more easily detected. In order to identify these mutants, the population of plants would be inoculated with a strain of powdery mildew, for example *Erysiphe cichoracearum* or *E. cruciferarum* strain UEA1. After a suitable period of incubation (e.g., 5–10 days), plants would then be screened for phenotype of the edr1 mutant: the development of distinct necrotic and collapsed regions on the leaves. That the phenotype is caused by an edr1 mutation is then established by molecular means well known in the art. Species contemplated to be screened with this approach include but are not limited to: aster, barley, begonia, beet, cantaloupe, carrot, chrysanthemum, clover, corn, cucumber, delphinium, grape, lawn and turf grasses, lettuce, pea, peppermint, rice, rutabaga, sugar beet, tomatillo, tomato, turnip, wheat, and zinnia.

B. Isolation of EDR1 Genes

A gene can be defined by its mapped position in the plant genome. Although the chromosomal position of the gene can change dramatically, the position of the gene in relation to its neighbor genes is often highly conserved (Lagercrantz et al., 1996, Plant J. 9:13–20). This conserved micro-colinearity can be used to isolate the EDR1 gene from distantly related plant species. In accordance with the present invention, the screening of genes and markers that flank EDR1 on the chromosome are known and are further present on the BAC clone of the *Arabidopsis* genome (BAC F22013, Genbank locus AC003981). These genes and markers can be used to isolate the EDR1 gene in their midst, or to confirm the identity of an isolated EDR1 nucleic acid (described below). For example, the various coding sequences can be used to design probes to isolate the EDR1 gene on BAC clones or to map the chromosomal location of the EDR1 gene using recombination frequencies. Additionally, genes highly homologous to those on *Arabidopsis* BAC F22013 are already known in other species, and these homologous genes may be used to locate EDR1 in these genomes. There are several versions of these procedures, and all will be well known to those skilled in the art.

C. Isolation of EDR1 Nucleic Acid Molecules

Nucleic acid molecules encoding the EDR1 protein may be isolated from *Arabidopsis* or any other plant of interest using methods well known in the art. Nucleic acid molecules from *Arabidopsis* may be isolated by screening *Arabidopsis* cDNA or genomic libraries with oligonucleotides designed to match the *Arabidopsis* nucleic acid sequence of EDR1 gene (SEQ ID NO:1). In order to isolate EDR1-encoding nucleic acids from plants other than *Arabidopsis*, oligonucleotides designed to match the nucleic acids encoding the *Arabidopsis* EDR1 protein may be likewise used with cDNA or genomic libraries from the desired species. If the EDR1 gene from a species is desired, the genomic library is screened. Alternately, if the protein coding sequence is of particular interest, the cDNA library is screened. In positions of degeneracy, where more than one nucleic acid residue could be used to encode the appropriate amino acid residue, all the appropriate nucleic acids residues may be incorporated to create a mixed oligonucleotide population, or a neutral base such as inosine may be used. The strategy of oligonucleotide design is well known in the art (see also Sambrook et al.).

Alternatively, PCR (polymerase chain reaction) primers may be designed by the above method to encode a portion of the *Arabidopsis* EDR1 protein, and these primers used to amplify nucleic acids from isolated cDNA or genomic DNA. In a preferred embodiment, the oligonucleotides used to isolate EDR1 nucleic acids are designed to encode sequences conserved in *Arabidopsis* EDR1 (SEQ ID NO:2), tomato TCTR2 (SEQ ID NO:4), rice EDR1 (SEQ ID NO:6), and barley EDR1 (SEQ ID NO:10), but not *Arabidopsis* CTRL (SEQ ID NO:3). In a particularly preferred embodiment, the sequences marked by arrows on FIG. 4, AVKKFLDQD and DPNLRPSFA (SEQ ID NOS:7 and 8) are used to design oligonucleotides and probes.

In accordance with the present invention, nucleic acids having the appropriate sequence homology with an *Arabidopsis* EDR1 nucleic acid molecule may be identified by using hybridization and washing conditions of appropriate stringency. For example, hybridizations may be performed, according to the method of Sambrook et al. (1989, supra), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° in 1×SSC and 1% SDS, changing the solution every 30 minutes.

One common formula for calculating the stringency conditions required to achieve hybridization between nucleic acid molecules of a specified sequence homology (Sambrook et al., 1989, supra) is:

$$T_m = 81.5° C. + 16.6 \text{Log } [Na+] + 0.41(\% G+C) - 0.63 (\% \text{ formamide}) - 600/\#bp \text{ in duplex}$$

As an illustration of the above formula, using [N+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. In a preferred embodiment, the hybridization is at ~37° C. and the final wash is at 42° C., in a more preferred embodiment the hybridization is at 42° and the final wash is at 50°, and in a most preferred embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable *E. coli* host cell.

*Arabidopsis* EDR1 nucleic acid molecules of the invention include DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule encoding the protein of the present invention. Such oligonucleotides are useful as probes for detecting *Arabidopsis* EDR1 genes or transcripts.

D. Engineering Plants to Alter EDR1 Activity

While the edr1 null mutant of the present invention is a naturally occurring mutant, any plant may be transgenically engineered to display a similar phenotype. While the natural edr1 mutant has lost the functional product of the EDR1 gene due to a premature stop codon in its coding sequence, a transgenic plant can be made that also has a similar loss of the EDR1 product. This approach is particularly appropriate to plants with high ploidy numbers, including but not limited to wheat.

A synthetic null mutant can be created by a expressing a mutant form of the EDR1 protein to create a "dominant negative effect". While not limiting the invention to any one mechanism, this mutant EDR1 protein will compete with wild-type EDR1 protein for interacting proteins in a transgenic plant. By over-producing the mutant form of the protein, the signaling pathway used by the wild-type EDR1 protein can be effectively blocked. Examples of this type of "dominant negative" effect are well known for both insect and vertebrate systems (Radke et al, 1997, Genetics 145: 163–171; Kolch et al., 1991, Nature 349:426–428). In a preferred embodiment, the mutant protein is produced by mutating the coding sequence corresponding to several residues in the kinase domain of EDR1 (amino acids 750–1015, Hanks et al., 1988, Science 241:42–52). In a particularly preferred embodiment, the coding sequence corresponding to the lysine residue at position 778 of SEQ ID NO:2 (which is conserved in all known kinases and required for kinase function) is mutated to code for a different, preferably non-similar, amino acid residue.

A second kind of synthetic null mutant can be created by inhibiting the translation of the EDR1 mRNA by "post-transcriptional gene silencing". The EDR1 gene from the species targeted for down-regulation, or a fragment thereof, may be utilized to control the production of the encoded protein. Full-length antisense molecules can be used for this purpose. Alternatively, antisense oligonucleotides targeted to specific regions of the EDR1-encoded RNA that are critical for translation may be utilized. The use of antisense molecules to decrease expression levels of a pre-determined gene is known in the art. Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al., 1998, PNAS 95:13959–13964). In a preferred embodiment, part or all of the EDR1 coding sequence antisense strand is expressed by a transgene. In a particularly preferred embodiment, hybridizing sense and antisense strands of part or all of the EDR1 coding sequence are transgenically expressed.

A third type of synthetic null mutant can also be created by the technique of "co-suppression". Plant cells are transformed with a copy of the endogenous gene targeted for repression. In many cases, this results in the complete repression of the native gene as well as the transgene. In a preferred embodiment, the EDR1 gene from the plant species of interest is isolated and used to transform cells of that same species.

Transgenic plants displaying enhanced EDR1 activity can also be created. This is accomplished by transforming plant cells with a transgene that expresses part of all of an EDR1 coding sequence, or a sequence that encodes the either the EDR1 protein or a protein functionally similar to it. In a preferred embodiment, the complete EDR1 coding sequence is transgenically over-expressed. In a particularly preferred embodiment, the coding sequence corresponding to the kinase domain of EDR1 is over-expressed.

Transgenic plants with one of the transgenes mentioned above can be generated using standard plant transformation methods known to those skilled in the art. These include, but are not limited to, *Agrobacterium* vectors, polyethylene glycol treatment of protoplasts, biolistic DNA delivery, UV laser microbeam, gemini virus vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., *Methods for Plant Molecular Biology* (Weissbach & Weissbach, eds., 1988); *Methods in Plant Molecular Biology* (Schuler & Zielinski, eds., 1989); *Plant Molecular Biology Manual* (Gelvin, Schilperoort, Verma, eds., 1993); and *Methods in Plant Molecular Biology—A Laboratory Manual* (Maliga, Klessig, Cashmore, Gruissem & Varner, eds., 1994).

The method of transformation depends upon the plant to be transformed. *Agrobacterium* vectors are often used to transform dicot species. *Agrobacterium* binary vectors include, but are not limited to, BIN19 (Bevan, 1984) and derivatives thereof, the pBI vector series (Jefferson et al., 1987), and binary vectors pGA482 and pGA492 (An, 1986) For transformation of monocot species, biolistic bombardment with particles coated with transforming DNA and silicon fibers coated with transforming DNA are often useful for nuclear transformation.

DNA constructs for transforming a selected plant comprise a coding sequence of interest operably linked to appropriate 51 (e.g., promoters and translational regulatory sequences) and 3' regulatory sequences (e.g., terminators). In a preferred embodiment, the coding region is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase (NOS) and octopine synthase (OCS) promoters.

Transgenic plants expressing a sense or antisense EDR1 coding sequence under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g. hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name a few.

Tissue specific and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired.

The coding region is also operably linked to an appropriate 3' regulatory sequence. In a preferred embodiment, the nopaline synthetase polyadenylation region (NOS) is used. Other useful 3' regulatory regions include, but are not limited to the octopine (OCS) polyadenylation region.

Using an *Agrobacterium* binary vector system for transformation, the selected coding region, under control of a constitutive or inducible promoter as described above, is linked to a nuclear drug resistance marker, such as kanamycin resistance. Other useful selectable marker systems include, but are not limited to: other genes that confer antibiotic resistances (e.g., resistance to hygromycin or bialaphos) or herbicide resistance (e.g., resistance to sulfonylurea, phosphinothricin, or glyphosate).

Plants are transformed and thereafter screened for one or more properties, including the lack of EDR1 protein, EDR1 mRNA, or enhanced resistance to plant pathogens, in particular powdery mildew fungi, the *Erysiphe* spp., and most particularly *E. cichoracearum* and *E. cruciferarum*. It should be recognized that the amount of expression, as well as the tissue-specific pattern of expression of the transgenes in transformed plants can vary depending on the position of their insertion into the nuclear genome. Such positional effects are well known in the art. For this reason, several nuclear transformants should be regenerated and tested for expression of the transgene.

Transgenic plants that exhibit one or more of the aforementioned desirable phenotypes can be used for plant breeding, or directly in agricultural or horticultural applications. Plants containing one transgene may also be crossed with plants containing a complementary transgene in order to produce plants with enhanced or combined phenotypes.

E. In Vivo Synthesis of the EDR1 Protein

The availability of amino acid sequence information, such as the full length sequence in SEQ ID NO: 2, enables the preparation of a synthetic gene that can be used to synthesize the *Arabidopsis* EDR1 protein in standard in vivo expression systems, or to transform different plant species. The sequence encoding *Arabidopsis* EDR1 from isolated native nucleic acid molecules can be utilized. Alternately, an isolated nucleic acid that encodes the amino acid sequences of the invention can be prepared by oligonucleotide synthesis. Codon usage tables can be used to design a synthetic sequence that encodes the protein of the invention. In a preferred embodiment, the codon usage table has been derived from the organism in which the synthetic nucleic acid will be expressed. For example, the codon usage for pea (*Pisum sativum*) would be used to design an expression DNA construct to produce the *Arabidopsis* EDR1 in pea. Synthetic nucleic acid molecules may be prepared by the phosphoramadite method employed in the Applied Biosystems 38A DNA Synthesizer or similar devices, and thereafter may be cloned and amplified in an appropriate vector.

The availability of nucleic acids molecules encoding the *Arabidopsis* EDR1 enables production of the protein using in vivo expression methods known in the art. According to a preferred embodiment, the protein may be produced by expression in a suitable expression system. The EDR1 protein of the present invention may also be prepared by in vitro transcription and translation of either native or synthetic nucleic acid sequences that encode the proteins of the present invention. While in vitro transcription/translation is not the method of choice for preparing large quantities of the protein, it is ideal for preparing small amounts of native or mutant proteins for research purposes, particularly since in vitro methods allow the incorporation of radioactive nucleotides such as $^{35}$S-labeled methionine. The EDR1 proteins of the present invention may be prepared by various synthetic methods of peptide synthesis via condensation of one or more amino acid residues, in accordance with conventional peptide synthesis methods. The EDR1 produced by native cells or by gene expression in a recombinant procaryotic or eukaryotic system may be purified according to methods known in the art.

F. Antibodies Immunospecific for EDR1

The present invention also provides antibodies that are immunologically specific to the *Arabidopsis* EDR1 of the invention. Polyclonal antibodies may be prepared according to standard methods. In a preferred embodiment, monoclonal antibodies are prepared, which are specific to various epitopes of the protein. Monoclonal antibodies may be prepared according to general methods of Köhler and Milstein, following standard protocols. Polyclonal or monoclonal antibodies that are immunologically specific for the *Arabidopsis* EDR1 can be utilized for identifying and purifying EDR1 from *Arabidopsis* and other species. For example, antibodies may be utilized for affinity separation of proteins for which they are specific or to quantify the protein. Antibodies may also be used to immunoprecipitate proteins from a sample containing a mixture of proteins and other biological molecules.

IV. Use of EDR1 Nucleic Acids, EDR1 Proteins and Antibodies, edr1 Mutants, and Transgenic Plants A. Uses of EDR1 Nucleic Acids.

EDR1 nucleic acids may be used for a variety of purposes in accordance with the present invention. DNA, RNA, or fragments thereof may be used as probes to detect the presence and/or expression of EDR1 genes. Methods in which EDR1 nucleic acids may be utilized as probes for such assays include, but are not limited to: (1) in situ hybridization; (2) Southern hybridization (3) Northern hybridization; and (4) assorted amplification reactions such as polymerase chain reactions (PCR).

The EDR1 nucleic acids of the invention may also be utilized as probes to identify related genes from other plant species. As is well known in the art, hybridization stringencies may be adjusted to allow hybridization of nucleic acid probes with complementary sequences of varying degrees of homology. As described above, EDR1 nucleic acids may be used to advantage to produce large quantities of substantially pure EDR1, or selected portions thereof. The EDR1 nucleic acids can be used to identify and isolate further members of this novel disease resistance signal transduction pathway in vivo. A yeast two hybrid system can be used to identify proteins that physically interact with the EDR1 protein, as well as isolate their nucleic acids. In this system, the sequence encoding the protein of interest is operably linked to the sequence encoding half of a activator protein. This construct is used to transform a yeast cell library which has been transformed with DNA constructs that contain the coding sequence for the other half of the activator protein operably linked to a random coding sequence from the organism of interest. When the protein made by the random coding sequence from the library interacts with the protein of interest, the two halves of the activator protein are physically associated and form a functional unit that activates the reporter gene. In accordance with the present invention, all or part of the *Arabidopsis* EDR1 coding sequence may be operably linked to the coding sequence of the first half of the activator, and the library of random coding sequences may be constructed with cDNA from *Arabidopsis* and operably linked to the coding sequence of the second half of the activator protein. Several activator protein/reporter genes are customarily used in the yeast two hybrid system. In a preferred embodiment, the bacterial repressor LexA DNA-binding domain and the Gal4 transcription activation domain fusion proteins associate to activate the LacZ reporter gene (see Clark et al., 1998, PNAS 95:5401–5406). Kits for the two hybrid system are also commercially available from Clontech, Palo Alto Calif., among others.

B. Uses of EDR1 Proteins and Antibodies:

The EDR1 proteins of the present invention can be used to identify molecules with binding affinity for EDR1, which are likely to be novel participants in this resistance pathway. In these assays, the known protein is allowed to form a physical interaction with the unknown binding molecule(s), often in a heterogenous solution of proteins. The known protein in complex with associated molecules is then isolated, and the nature of the associated protein(s) and/or other molecules is determined.

Antibodies that are immunologically specific for EDR1 may be utilized in affinity chromatography to isolate the EDR1 protein, to quantify the EDR1 protein utilizing techniques such as western blotting and ELISA, or to immunoprecipitate EDR1 from a sample containing a mixture of proteins and other biological materials. The immuno-precipitation of EDR1 is particularly advantageous when utilized to isolate affinity binding complexes of EDR1, as described above.

C. Uses of edr1 Mutants.

The edr1 mutants of the invention display enhanced disease resistance to plant pathogens of both fungal and bacterial origin, and therefore can be used to improve crop and horticultural plant species. The edr1 mutants are particularly resistant to powdery mildew. Such mutants will therefore be particularly useful when isolated from crop and horticultural varieties in which an infection by powdery mildew-inducing fungi, such as *Erisyphe* spp., *Oidium* spp. and *Uncinula necator*, results in loss. Plants species contemplated in regard to this invention include, but are not limited to: aster, barley, begonia, beet, cantaloupe, carrot, chrysanthemum, clover, corn, cucumber, delphinium, grape, lawn and turf grasses, lettuce, pea, peppermint, rice, rutabaga, sugar beet, tomatillo, tomato, turnip, wheat, and zinnia.

The edr1 mutants have a broad-based resistance to *Erysiphe*, also encompassing the species *E. cruciferarum*. It is therefore contemplated that the edr1 mutants will exhibit broad-spectrum resistance against a wide range of *Erysiphe* species and other members of *Erysiphales*. Such species include, but are not limited to, *E. graminis, E. polygoni, E. betae, E. heraclei, E. pisi, E. trifolii*, the *Oidium* species, particularly *O. lycopersicon*, and the *Uncinula* species, particularly *U. necator*. The mechanism of resistance involves the repression of fruiting body formation, and since pathogenic fungi in general have very similar methods infection, it is contemplated that these mutants will be more resistant to many forms of pathogenic fungi. Other fungal species considered in connection with the invention include, but are not limited to, biotrophic fungal species, such as those causing downy mildew and rust diseases.

The enhanced resistance exhibited by the mutants of the invention extends also to bacterial plant pathogens. The edr1 mutants exhibit increased resistance to *Pseudomonas syringae* and *Pseudomonas syringae* pv maculicola M2. This broad spectrum resistance to *Pseudomonas* strains is very likely to extend to all *Pseudomonas* species. The edr1 mutants are contemplated for use in providing resistance to all *Pseudomonas* species, including but not limited to, *P. cichorii, P. coronafaciens, P. lacrymans, P. marginata* and numerous *P. syringae* pathovars. It is contemplated that edr1 mutations will be selected from plant species that are susceptible to *Pseudomonas* infection: blueberry, english laurel, lilac, willow, apple, pear, raspberry, lettuce, oats, cucumber, gladiolus, bean, pea, cherry, maple, prune, plum, tomato, soybean, wheat, barley, rice and corn, among others.

The edr1 mutants exhibit a heightened induction of normal resistance pathways. It is therefore contemplated that these mutants will have enhanced resistance to a myriad of plant pathogens in addition to the specific fungal and bacterial species mentioned heretofore.

The edr1 mutants of the invention can be used to identify and isolate additional members of this disease resistance pathway. Mutations that, when combined with edr1, suppress the edr1 phenotype, are likely to interact directly with EDR1, or to compensate in some other way for the loss of EDR1 function.

E. Uses of EDR1 Transgenic Plants.

The transgenic plants of the invention are particularly useful in conferring the edr1 phenotype to many different plant species. In this manner, a host of plant species with enhanced disease resistance can be easily made, to be used as breeding lines or directly in commercial operations. Such plants can have uses as crop species, or for ornamental use.

A plant that has had functional EDR1 transgenically depleted will exhibit the same enhanced resistance as the edr1 mutants. It is therefore contemplated that transgenic edr1-phenotype plants will be used with the same aforementioned pathogens and plant species as the edr1 mutants. A transgenic approach is advantageous because it allows edr1-phenotype plants to be created quickly, without time-consuming mutant generation, selection, and back-crossing. Transgenically created edr1-phenotype plants have special utility in polyploid plants, such as wheat, where recessive mutations are difficult to detect.

A plant that has had functional EDR1 increased may have delayed senescence compared to wild-type plants. Plants with delayed senescence will be extremely valuable to agriculture and horticulture by allowing plants to flower, leaves to remain productive, and harvested fruits, vegetables and flowers to remain fresh for longer periods of time. It may also allow fruit with abscission zones such as tomato to accumulate sugars from a longer period of time.

The following examples are provided to describe the invention in greater detail. They are intended to illustrate, not to limit, the invention.

EXAMPLE 1

Isolation and Characterization of the edr1 Mutant in *Arabidopsis*

Methods

Bacterial and Fungal Strains and Media. Strain DC3000 of *Pseudomonas syringae* pv *tomato* was obtained from D. Cuppels (Agricultural Canada-Research Center, London, Ontario, Canada) and strain M4 of *P. s.* pv *maculicola* was provided by J. Dangl (University of North Carolina, Chapel Hill). Both *P. syringae* strains were cultured at 30° C. on either King's medium B (King et al., 1954, J. Lab. Clin. Med. 44:301–307) or trypticase soy agar (TSA; Becton Dickinson, Cockeysville, Md.) supplemented with 100 mg/L rifamycin (Sigma). Strain UCSC of *Erysiphe cichoracearum* was kindly provided by S. Sommerville (Carnegie Institute of Washington, Stanford, Calif.) and was maintained on *Arabidopsis* accession Columbia (Col-0) by brushing diseased plants onto new plants. Inoculated plants were maintained under a 14-hr day length at 22° C.

Seed Sources. Wild-type *Arabidopsis thaliana* ecotype Col-0 seed was obtained from B. J. Staskawicz (University of California, Berkeley). Mutagenized seed ($M_2$ generation) was obtained from Lehle Seeds (Round Rock, Tex.; fast-neutron mutagenized) or M. Estelle (Indiana University, Bloomington; ethyl methanesulfonate mutagenized and γ-irradiated). In all cases, $M_1$ generation seeds were mutagenized, planted and allowed to self-pollinate to generate the $M_2$ population. $M_2$ populations were bulked from approximately 500 $M_1$ plants. The edr1 mutant was isolated from the γ-irradiated population. Third and fourth generations ($M_3$ and $M_4$) of the edr1 mutant were used interchangeably for phenotypic analyses and crosses.

*Arabidopsis* Growth and Bacterial Inoculation. *Arabidopsis* seeds were sown in 4-inch-round pots filled with Perlite Plug Mix (Grace Sierra, Milpitas, Calif.). Pots were covered with 1.3-mm nylon mesh (window/door screen), and plants were allowed to grow through the screen. Seeded pots were covered and held at 4° C. for 3 days before being placed in growth rooms under a 9-hr day length (100 to 150 microE·m–2·sec$^{-1}$ of light) at 24° C. Covers were removed after the seeds sprouted and the first true leaves were emerging.

Adult plants (4 to 6 weeks after sowing) were inoculated by dipping whole rosettes in a suspension of $1\times10^9$ colony-forming units of *P. s. tomato* DC3000 per ml suspended in 10 mM $MgCl_2$ supplemented with 0.025% (v/v) L77 Silwet (OSI Specialties, Danbury, Conn.). Inoculated plants were maintained for about 24 hr with humidity domes under growth conditions described above. Disease symptoms were scored 4 to 5 days after inoculation.

To monitor bacterial growth inside plant leaves, adult plants (4 to 6 weeks after sowing) were vacuum infiltrated with $1\times10^5$ colony-forming units per ml of *P. s. maculicola* M4. Bacterial suspensions contained 0.01% L77 Silwet and 10 mM $MgCl_2$. At specific time points, samples were removed from rosette leaves using a number 2 cork borer (three discs per sample) and macerated in 200 µl of 10 mM $MgCl_2$. Dilutions were made in 10 mM $MgCl_2$ and plated on trypticase soy agar containing 100 mg/L rifamycin and incubated at 30° C. Colonies were counted 48 hr later.

*E. cichozacearum* Inoculation and Histology. *E. cichoracearum* actively growing on Col-0 plants (7–10 days post-inoculation) was used as an inoculum. To inoculate plants, diseased plants were used to brush healthy plants, thus passing spores onto the new plants.

Fungal structures and dead plant cells were stained by collecting leaves and boiling for 2 min in alcoholic lactophenol trypan blue (20 ml of ethanol, 10 ml of phenol, 10 ml of water, 10 ml of lactic acid (83%), and 10 mg of trypan blue). Stained leaves were cleared in chloral hydrate (2.5 g dissolved in 1 ml of water) overnight at room temperature (Koch and Slusarenko, 1990, Plant Cell, 2:437–445). Cleared leaves were mounted under coverslips in 50% glycerol.

Autofluorescence and callose were detected as described by Adam and Sommerville (1995, Plant J. 9:341–356). To observe all tissues, leaves were mounted under coverslips with 50% glycerol and observed with an Axiophot Microscope (Carl Zeiss, Oberkochen, Germany). Autofluorescence and callose fluorescence were analyzed using a 4',6-diamidino-2-phenylindole filter setting.

Quantification of *E. cichoracearum* Growth. The percentage of germinating spores was determined 1 day after inoculation. Germination was defined as the presence of a germ tube. Hyphal length (3 days and 7 days post inoculation) and conidiophore number (7 days post inoculation) were obtained from a minimum of six trypan blue-stained leaves collected from separate experiments. Microscopic images (described above) were captured and digitized using a ZVS-3C75DE 3 CCD video camera (Carl Zeiss) and PowerTower Pro 180 computer (PowerComputing, Round Rock, Tex.). Digitized images were viewed and printed using Adobe Photoshop software (Adobe Systems, San Jose, Calif.). Hyphal length at 3 days post inoculation was measured on the printed images and converted to actual measurements by comparing to an image of a slide micrometer. To calculate conidiophores per millimeter of hyphae at 7 days post inoculation, hyphal length was estimated using a 50-mm grid on the printed image as described by Olson (1950, Trans. Am. Microscop. Soc. 69:272–279). Conidiophores on the printed image were counted directly. Fields with approximately equal hyphal density were chosen to assure equal sampling.

Analysis of Pathogenesis-Related Gene Expression. RNA was purified from frozen leaf tissue using a phenol-chloroform-guanidine hydrochloride extraction procedure (Logemann et al., 1987, Anal. Biochem. 163:16–20). RNA concentration was determined spectrophotometrically by absorbance at 260 nm. Twenty-five-microgram samples of total RNA were separated by electrophoresis through a formaldehyde agarose (1.5%) gel (Sambrook et al., 1989, supra). RNA was transferred from the gel to a nylon membrane and hybridized to $^{32}$P-dATP-labeled DNA probes following the manufacturer's instructions (Hybond N, Amersham). Probes were generated using a Random Primed DNA labeling kit (Boehringer Mannheim). DNA templates for probes were generated by polymerase chain reaction amplification of *Arabidopsis* genomic DNA (BGL2, PR-5, and ubiquitin [UBQ5]) or amplification from a cDNA clone (PR-1; Uknes, et al., 1992, Plant Cell, 4:645–656) using published primers (Glazebrook et al., 1996, Genetics 143: 973–982). Hybridization was quantified using a Molecular Dynamics (Sunnyvale, Calif.) PhosphorImager. Values for PR-1 and BGL2 hybridization were normalized for unequal loading using values obtained from the UBQ5 hybridization. Images were obtained by exposing the membrane to X-ray film (Fuji Film RX, Fisher Scientific).

Genetic Analysis. *Arabidopsis* mutant edr1 was crossed to accession Landsberg erecta (Ler). The $F_1$, $F_2$, and $F_3$ plants were scored for the mutant phenotype after dusting with *E.*

*cichoracearum* spores. Resistant $F_2$ plants were selected for generation of $F_3$ families, which were used to confirm $F_2$ mutant phenotypes. DNA for analysis of molecular markers was collected from one or two inner rosette leaves of resistant $F_2$ plants using a hexadecyltri-methylammonium bromide (CTAB) extraction procedure (Bisgrove et al., 1994, Plant Cell, 6:927–933). Simple sequence length polymorphism (SSLP) and codominant amplified polymorphic sequence (CAPS) markers were amplified using the polymerase chain reaction (Konieczny and Ausubel, 1993, Plant J. 4:403–410; Bell and Ecker, 1994, Genomics 19:137–144). All primers for SSLP and CAPS markers were purchased from Research Genetics (Hunstville, Ala.). Amplified products were resolved on a 4% NuSieve gel (3:1 NuSieve: Seakem LE, FMC, Rockland, Me.).

Results

Isolation of *Arabidopsis* Mutants Resistant to Disease. *Arabidopsis* accession Columbia (Col-0) is susceptible to *P. s. tomato* DC3000. Disease symptoms develop on rosette leaves 4 to 5 days after inoculation and appear as gray lesions surrounded by chlorosis (Whalen et al., 1991, Plant Cell, 3:49–59). To identify *Arabidopsis* mutants with reduced susceptibility, we inoculated mutagenized Col-0 plants ($M_2$ generation) with *P. s. tomato* DC3000 and scored for disease lesion severity 4 to 5 days later. Plants were inoculated with a high dose of *P. s. tomato* DC3000 ($1 \times 10^9$ colony forming units per ml), facilitating the identification of living resistant plants because at this concentration susceptible plants frequently died. Living plants displaying a decrease in the severity of disease symptoms were selected for further analysis. Reduced disease symptoms included fewer leaves showing disease, smaller lesions, and a lack of lesions on inner-rosette leaves. Approximately 25,000 mutagenized Col-0 plants were screened, and 78 putative mutants were selected. The mutant phenotype of decreased disease symptoms was found to be heritable in 36 of the 78 plants selected.

To determine whether reduced symptoms correlated with reduced bacterial growth, we quantified bacterial numbers in leaves over a 4-day period. Of the 36 mutants, 25 showed a reduction in bacterial growth in the leaves as compared to wild-type Col-0 plants.

To eliminate mutants that were constitutively expressing SAR, we analyzed expression of the PR-1 gene in uninoculated plants. PR-1 gene expression was assayed using RNA gel blot analysis. Of 19 mutants analyzed (six were not tested), six displayed strong expression of PR-1, seven displayed weak expression, and six did not have detectable expression of PR-1. The latter six mutants represent a novel class as they are less susceptible to a virulent pathogen by a mechanism independent of constitutive expression of SAR. These mutants have been termed enhanced disease resistant (edr).

To determine whether any of the edr mutants displayed broad spectrum disease resistance, we tested them for resistance to *E. cichoracearum*, causal agent of powdery mildew. *Arabidopsis* accession Col-0 is susceptible to the UCSC strain of *E. cichoracearum*, developing the macroscopic disease symptoms of powdery mildew (a white powder resulting from production of asexual spores; Adam and Somerville, 1996, supra) on the leaves 7–10 days after inoculation. One of the six edr mutants displayed resistance to *E. cichoracearum*, developing almost no visible powder. We performed a phenotypic and genetic analysis of this mutant, which we have designated edr1.

Decreased Susceptibility of edr1 Plants to Bacterial Pathogens. Decreased susceptibility to *P. s. tomato* DC3000 was a criterion for selecting the edr mutants. Edr1 plants displayed fewer disease lesions than wild-type Col-0 plants after inoculation with *P. s. tomato*. At 2 days post inoculation, the level of *P. s. tomato* DC3000 in edr1 leaves was significantly less than level of *P. s. tomato* DC 3000 in wild-type Col-0 leaves FIG. 1A; t=3.01, P=0.0395). While the difference in bacterial growth between edr1 and Col-0 plants was small, the difference in disease lesion development was more striking. These results suggested a relationship between bacterial growth from 0–2 days post inoculation and the severity of disease lesions.

Figure 1B:
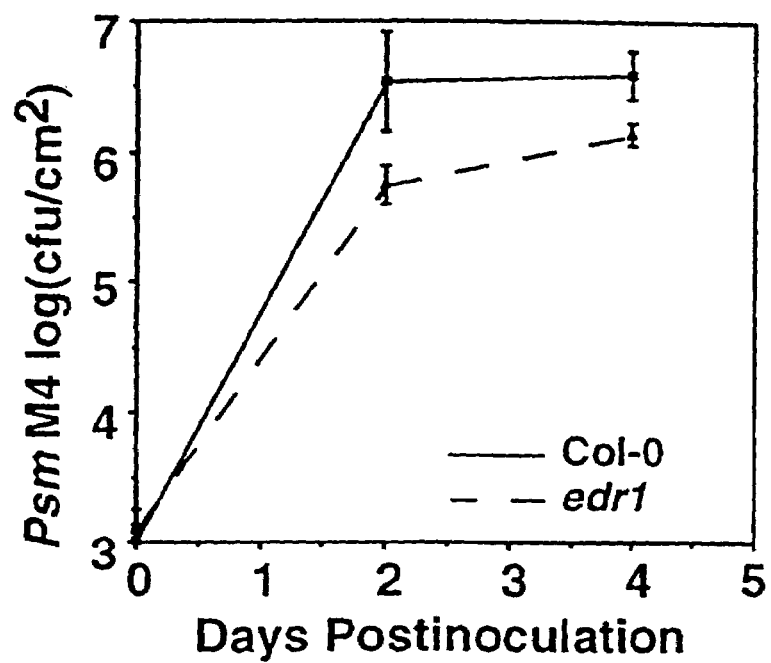
FIG. 1B. Time course of *P.S. maculicola* M4 growth in *Arabidopsis* leaves.

To determine whether the edr1 mutant was less susceptible to a second bacterial pathogen, we inoculated edr1 and wild-type Col-0 plants with *P. s. maculicola* strain M4 and examined both lesion development and bacterial growth in plant leaves over 4 days. *Pseudomonas s. maculicola* M4 is virulent on Col-0 causing disease symptoms similar to those of *P. s. tomato* DC3000 (gray lesions surrounded by chlorosis). The edr1 plants developed less severe disease symptoms than wild-type Col-0 after inoculation with *P. s. maculicola* M4, suggesting decreased susceptibility to *P. s. maculicola* M4. Analysis of *P. s. maculicola* M4 growth in edr1 plants also indicated decreased susceptibility (FIG. 1B), however this difference was not statistically significant (t=1.97, P=0.12).

*E. cichoracearum* is arrested at a late stage of the infection process in edr1 plants. The infection process of *E. cichoracearum* on *Arabidopsis* is known. Spores first produce appressorial germ tubes that penetrate the underlying epidermal cells. Inside the epidermal cells the fungus forms a haustorium, which is a bag-like invagination surrounded by host cell plasma membrane. Fungal development then proceeds via formation of secondary hyphae and haustoria and terminates with formation of conidiophores (stalks of asexual spores) 5 to 7 days after infection. It is these conidiophores that produce the "powdery" appearance for which the disease is named.

Approximately 7 days after inoculation with asexual spores of *E. cichoracearum*, wild-type *Arabidopsis* plants displayed abundant conidiophores (visible white powder) on mature plant leaves. The edr1 plants displayed strong disease resistance to *E. cichoracearum*. Starting 6 days post inoculation, the mature leaves of edr1 plants became slightly chlorotic then developed distinct necrotic and collapsed regions. Over the next 3 days the necrosis spread to consume large portions of the leaf. During this same time period, wild-type Col-0 leaves displayed abundant conidiophores with some chlorosis but no necrosis. Visible necrosis in edr1 plants began just prior to the development of visible powder on wild-type Col-0 plants. The edr1 mutant developed only small scattered patches of powder.

To determine the stage of fungal development that was affected on edr1 plants, infected leaves at various time points were stained with trypan blue, which detects both fungal structures and dead plant cells (Koch and Slusarenko, 1990, Plant Cell 2:437–445). As shown in Table 2, on both Col-0 and edr1 leaves, approximately 60% of the spores developed appressorial germ tubes 1 day after inoculation. By 3 days after inoculation, *E. cichoracearum* spores developed extensive branched hyphae with secondary germ tubes that invaded underlying epidermal cells. The average length of hyphae did not differ between germlings on edr1 leaves and Col-0 leaves (Table 2).

TABLE 2

Erysiphe development on wild-type Col-O and edr1 leaves.

| stage of development | Col-0 | edr1 |
|---|---|---|
| germination[a] | 65.3% (49) | 66.0% (50) |
| hyphal length[b] | 1.99 ± 0.2 mm (16) | 1.86 ± 0.2 mm (18) |
| conidiophores/mm hyphae[c] | 2.47 ± 0.34 (7) | 0.38 ± 0.12 (12) |

[a]Asexual spore germination measured 1 day post-inoculation. Values are expressed as the mean ± SE; (n) = number of germlings.

By 5 days post inoculation *E. cichoracearum* developed extensive hyphal growth that nearly covered the leaf surface on both edr1 and wild-type Col-0 plants. By day 7, *E. cichoracearum* developed abundant conidiophores on wild-type Col-0 plants; however, these structures were severely reduced in number on edr1 leaves (Table 2). The conidiophores that were present on edr1 leaves often were not septated and appeared to be under-developed compared to those on wild-type Col-0 leaves at the same time point. These observations indicate *E. cichoracearum* development is arrested just prior to formation of conidiophores, a relatively late stage in the infection process.

Defense Responses Are More Strongly Induced In edr1 Plants. The necrotic patches observed on edr1 plants after infection with *E. cichoracearum* indicated that cell death was occurring. Therefore, we determined whether edr1 plants displayed microscopic patches of dead cells prior to pathogen exposure as has been reported for mlo and lesions simulating disease (lsd) mutants. Dead cells were visualized using trypan blue staining. No difference between edr1 and wild-type plants was observed prior to pathogen exposure. Five days after inoculation with *E. cichoracearum*, both edr1 and wild-type Col-0 plants displayed small scattered groups of dead cells that did not correlate with presence of fungal hyphae. Leaves from edr1 plants, however, contained large clusters of dead mesophyll cells (more than 30 cells) that were invariably associated with areas of dense hyphal growth. Large clusters of dead cells were not observed in wild-type Col-0 leaves.

Plant cells undergoing an HR accumulate callose and autofluorescent compounds in the cell wall. To determine whether the necrosis observed in edr1 plants shared the biochemical properties of an HR, we assayed infected leaves for deposition of autofluorescent compounds and for callose. Both wild-type Col-0 and edr1 plants displayed punctate staining of callose in the cell walls of epidermal cells approximately 3 days post inoculation; however, only edr1 plants showed callose staining in large clumps of mesophyll cells. The bright punctate staining observed in epidermal cells of both Col-0 and edr1 plants is absent in noninoculated plant leaves and probably represents a collar of callose-containing plant material. It has been shown that susceptible and resistant plants respond to fungal penetration by generating a papilla at the infection site.

In susceptible plants, the fungus penetrates through the papillae that subsequently becomes a collar around the penetration peg. Callose deposition in the mesophyll cells of edr1 leaves is evident 3 days after inoculation with *E. cichoracearum*, which is prior to the appearance of dead cells. The pattern of autofluorescence was similar to that observed for callose. Autofluorescing mesophyll cells accumulated in edr1 leaves beginning 3 days post inoculation. Col-0 leaves showed only scattered epidermal cells autofluorescing at the same time point.

Analysis of PR Gene Expression. One of the criteria used to identify the edr1 mutant was the lack of constitutive PR-1 gene expression. It was possible, however, that the enhanced resistance of edr1 was mediated by a more rapid or stronger induction of SAR, or of SAR-associated genes other than PR-1. Therefore, we used RNA gel blot analysis to assay for expression of three SAR-associated genes during infection by *E. cichoracearum*.

Little to no PR-1 and BGL2 mRNA was detectable prior to inoculation, or 1 day after infection. By 3 days after infection, significant levels of PR-1 and BGL2 were observed in both wild type and edr1 plants. We quantified the levels of mRNA detected by using a PhosphorImager. The level of PR-1 message in edr1 leaves at day 3 was approximately four times higher than in Col-0 leaves. PR-1 and BGL2 transcript levels increased at days 5 and 7 after infection, but the relative difference between edr1 and wild-type plants was less. By day 7, PR-1 levels were higher in wild-type Col-0 than in edr1 -plants. Analysis of BGL2 and PR-5 transcript levels also revealed a small but reproducible increase in edr1 plants relative to wild type Col-0 on days 3 and 5 after inoculation.

Genetic Analysis of edr1. To determine the inheritance of the enhanced resistance phenotype, the edr1 mutant was crossed with *Arabidopsis* accession Landsberg erecta (Ler), which is susceptible *E. cichoracearum*. The $F_2$ progeny were inoculated with *E. cichoracearum* conidia and scored 7–9 days later for development of necrotic lesions and lack of visible powdery mildew. These two traits co-segregated, and behaved as a recessive mutation, producing approximately a 1:3 ratio of resistant-to-susceptible plants (85:266; $X^2=0.115$; $P>0.1$).

To obtain a chromosomal map position for the mutation in edr1 plants, a total of 1223 $F_2$ plants from the Ler cross were scored for *E. cichoracearum* resistance and 235 plants displaying resistance to *E. cichoracearum* were selected for mapping. DNA was isolated from the resistant $F_2$ plants and analyzed for linkage to SSLP and CAPS markers (Konieczny and Ausubel, 1993, supra; Bell and Ecker, 1994, supra). The edr1 mutation mapped 3.2 centiMorgans centromeric from the SSLP marker ATEAT1 (15 recombinant chromosomes) and 0.85 centiMorgans telomeric from the CAPS marker NCC1 (4 recombinant chromosomes) on chromosome 1.

Discussion

The edr1 mutant displays enhanced resistance to powdery mildew, but does not constitutively express pathogenesis related genes, such as PR-1 and BGL2. The latter observation indicates resistance is being conferred by a mechanism that differs from previously described *Arabidopsis* disease resistant mutants. Our data show that multiple defense responses are induced more rapidly in edr1 plants than in wild-type plants when infected with a virulent strain of powdery mildew. These observations suggest that the edr1 mutation leads to a "hair trigger" inducibility of these responses.

We obtained the edr1 mutant by screening for plants that displayed enhanced resistance to the bacterial pathogen *P. s. tomato* DC3000, suggesting that the edr1 mutation also enables a more rapid defense response against bacteria. However, the resistance to *P. s. tomato* DC3000 was variable. The edr1 mutant also displayed variable resistance to a second strain of *P. syringae*, *P. s. pv maculicola* M2. These observations suggest that edr1-mediated resistance to *P. syringae* may be influenced by environmental factors.

The difference in effect of the edr1 mutation on *P. syringae* infection compared to *E. cichoracearum* might be related to the different modes of infection of these pathogens. *P. syringae* colonizes the intercellular spaces of the leaf mesophyll, reaching maximum population levels within 2 to 3 days after infection. In contrast, *E. cichoracearum* remains on the leaf surface and does not produce spores until 6 to 7 days after infection.

To further evaluate the spectrum of resistance conferred by the edr1 mutation, the mutant was challenged with additional pathogens. The edr1 mutant was found to be resistant to a second species of *Erysiphe*, *E. cruciferarum* strain UEA1. This pathogen induced a resistance phenotype essentially the same as that induced by *E. cichoracearum*, including mesophyll cell death associated with a dramatic decrease in conidiophore production. This result suggests the edr1 mutation confers a broad-spectrum rather than race-specific resistance against powdery mildew.

Resistance to *E. cichoracearum* in edr1 plants is manifested at a relatively late stage in the infection. *Erysiphe cichoracearum* spores germinated on the leaf surface and developed extensive networks of secondary hyphae on both edr1 and wild-type Col-0 plants. Asexual reproduction was dramatically reduced on edr1 plants; both the number of conidiophores formed as well as the number of conidia that make up each conidiophore were decreased. These observations suggest that the edr1 resistance response affects the fungus primarily after onset of conidiophore formation at day 4.

Consistent with the observed effect on fungus development, we did not detect enhanced defense responses in edr1 plants until 3 days after infection with *E. cichoracearum*. The earliest response detected was deposition of callose and autofluorescent compounds in epidermal cells and underlying mesophyll cells. We also observed a slightly enhanced expression of PR genes at day 3; however, cell death was not observed until 5 days after inoculation.

In response to fungal infection, the defense mechanisms observed in edr1 plants are slow compared to that conferred by most classical disease resistance genes. For example, barley plants containing the Mla1 gene induce a single cell HR within 14 hr of infection by an avirulent strain of *Erysiphe graminis* f.sp. *hordei*, preventing the fungus from forming secondary hyphae (et al., 1995, Plant J. 7:959–968). Not all powdery mildew resistance genes confer a rapid HR, however. The resistance phenotype of edr1 plants to *E. cichoracearum* is similar to the phenotypes conferred by the Pm2 and pm5 genes of wheat, and the Mla3 and Mla7 genes of barley. These resistance genes affect powdery mildew growth after the development of secondary hyphae, but before conidiophore production, and are associated with the accumulation of large masses of dead mesophyll cells (Hyde and Colhoun, 1975, Phytopath. Z. 82:185–206; Boyd, et al., 1995, supra). In addition, plants with rapidly acting resistance genes occasionally allow fungal germlings to form secondary hyphae. Growth of such escapees is usually halted prior to conidiophore formation and is associated with mesophyll cell death (Hyde and Colhoun, 1975, supra).

The edr1 resistance phenotype shares some attributes with resistance mediated by the mlo mutation of barley. The mlo mutation is recessive and confers resistance to multiple races of *E. g. hordei*, but has no apparent effect on other pathogen species tested, such as *Puccinia hordei*, the causative agent of rust on barley (Jorgensen, 1992, supra; Wolter, et al., 1993, supra). Similarly, edr1 plants showed clear resistance to two species of powdery mildew, but variable resistance to bacterial pathogens. Unlike edr1, however, mlo resistance is associated with the formation of callose rich papillae that are thought to block penetration of the fungus into the initially infected epidermal cell (Aist et al., 1988, Physiol. Molec. Plant Pathol. 33:17–32; Wolter, et al., 1993, supra); secondary hyphae very rarely form on mlo plants. The edr1 mutation does not map to the same location as the Mlo-like *Arabidopsis* genes identified previously (Büschges, et al., 1997, Cell, 88:695–705).

EXAMPLE 2

Isolation and Analysis of the EDR1 Gene

Isolation of the EDR1 gene. The edr1 mutation was located on the genetic map of *Arabidopsis* by genetic linkage analysis (see Example 1). After identifying closely linked molecular markers, two overlapping bacterial artificial chromosome (BAC) clones were identified that genetically span the region containing edr1. EDR1 was therefore contained on one of these two BAC clones, F22013 and F7G19, which are publicly available clones generated as part of the ongoing *Arabidopsis* genome project. The complete DNA sequence of these two clones is available from the Genbank DNA database. Using this sequence information, additional molecular markers were generated that localized the EDR1 gene to an approximately 100 kilobase pair interval, most of which was contained on BAC clone F22013. Analysis of the DNA sequence in this interval revealed 25 potential protein coding genes. To determine which of these 25 genes encoded EDR1, candidate genes from our edr1 mutant were sequenced with the reasoning that the EDR1 gene should contain an alteration in its DNA sequence in the edr1 mutant plant. Candidate genes were amplified from the edr1 mutant using the polymerase chain reaction (PCR). DNA sequences of PCR products were determined using an ABI Dye Terminator FS kit protocol (Perkin-Elmer, Foster City, Calif.) on an ABI Prism 377 DNA sequencer.

Candidates were chosen based on the probability that mutations in such genes could lead to the observed edr1 phenotype. In particular, genes known to play a role in stress responses (e.g. superoxide dismutase) or in signal transduction (e.g. protein kinases and transcription factors) were focused on. Upon sequencing candidate gene F22013.21, which had similarity to MAP3 kinases (also known as "mitogen activated protein kinase kinase kinase"), a single nucleotide difference between the edr1 mutant and wild-type *Arabidopsis* was discovered. This gene was sequenced again from wild-type *Arabidopsis* plants to insure this nucleotide difference was correct. This nucleotide change produces a premature stop codon (codon 392 (TAC) is converted to a TAG (stop) codon), thus eliminating the C-terminal half of the protein, including the entire putative protein kinase domain (see SEQ ID NO:1). Such a mutation would be expected to render the EDR1 protein non-functional, which is consistent with the recessive nature of the edr1 mutation. Because this nucleotide change co-segregates with the edr1 phenotype, it is very likely that this MAP3 kinase represents EDR1. To prove this, a wild-type copy of the EDR1 gene was transformed into an edr1 mutant *Arabidopsis* plant using *Agrobacterium*-mediated transformation. Four out of five independent transgenic lines showed a restoration of a wild-type phenotype, indicating the indentified MAP3 kinase gene could rescue the edr1 mutant phenotype. Henceforth, this MAP3 kinase is referred to as the EDR1 protein.

Structural Analysis of the Predicted EDR1 Protein. The EDR1 protein sequence (SEQ ID NO:2) contains high similarity to a large number of protein kinases, which are proteins that can catalyze the addition of phosphate groups to other proteins. Many protein kinases are known to participate in signal relays, passing information from outside the cell to other sites within the cell ("signal transduction"). One of the proteins most similar to EDR1 is another *Arabidopsis* protein called CTR1 (SEQ ID NO:3). The similarity is highest in the putative kinase domain, but extends to other regions of the protein as well (FIG. 2). This similarity is informative, as a considerable amount is known about CTR1. Loss of function mutations in CTR1 result in induction of ethylene-induced responses. In other words, plants with null mutations in CTR1 behave as if they are being exposed to high levels of ethylene all the time. The CTRL protein functions to repress (i.e. keep off) these responses in the absence of ethylene. In the presence of ethylene, the CTR1 protein is inactivated, leading to the induction of these responses. The CTR1 protein is thus described as a negative regulator of the ethylene response pathway. The EDR1 protein may by analogy function as a negative regulator of specific defense response pathways. In the absence of functional EDR1 protein, these pathways are more easily induced by pathogens, leading to enhanced disease resistance.

The CTR1 protein has been shown to interact with a second protein known as ETR1, which is a receptor for the ethylene molecule. This interaction indicates that CTRL functions near the beginning of the signal relay between perception of ethylene and the activation of ethylene responses. The similarity between CTR1 and EDR1 suggests that EDR1 may also function near the beginning of a signal relay, perhaps activated by a pathogen molecule.

Homologs of EDR1 exist in Crop Species. The *Arabidopsis* EDR1 sequence has been used to identify homologs in rice and barley, and can be used to identify homologs in other crop plants. Once these homologous genes are identified they can be inactivated, thus creating edr1-like mutants that have enhanced disease resistance. A search of the Genbank DNA, protein, and expressed sequence tag (EST) databases reveals several strongly homologous genes. Although many genes show similarity to the kinase domain encoding portion of EDR1, one gene from tomato called TCTR2 (SEQ ID NO:4) shows extensive homology throughout the protein-coding region (FIG. 3), indicating that this gene encodes the tomato version of EDR1. Alignment of EDR1 and TCTR2 reveals numerous regions where the amino acid sequences are identical. Such regions may be used to design PCR primers to enable amplification of EDR1 homologs from other plant species.

In addition to TCTR2, EDR1 showed high similarity to an EST sequence from rice. Because EST sequences represent only partial sequences of the corresponding cDNA clones, this cDNA clone was obtained and the complete DNA sequence determined (SEQ ID NO:5). The rice EDR1 protein sequence (SEQ ID NO:6) is aligned with EDR1, TCTR2, and CTR1 in FIG. 4. The high degree of similarity between EDR1 and the protein encoded by the rice cDNA indicates that this cDNA corresponds to the rice version of EDR1. The protein sequence encoded by the rice cDNA is more similar to EDR1 and TCTR2 than any other sequences in the public databases, including CTR1 (Table 1).

Figure 4:
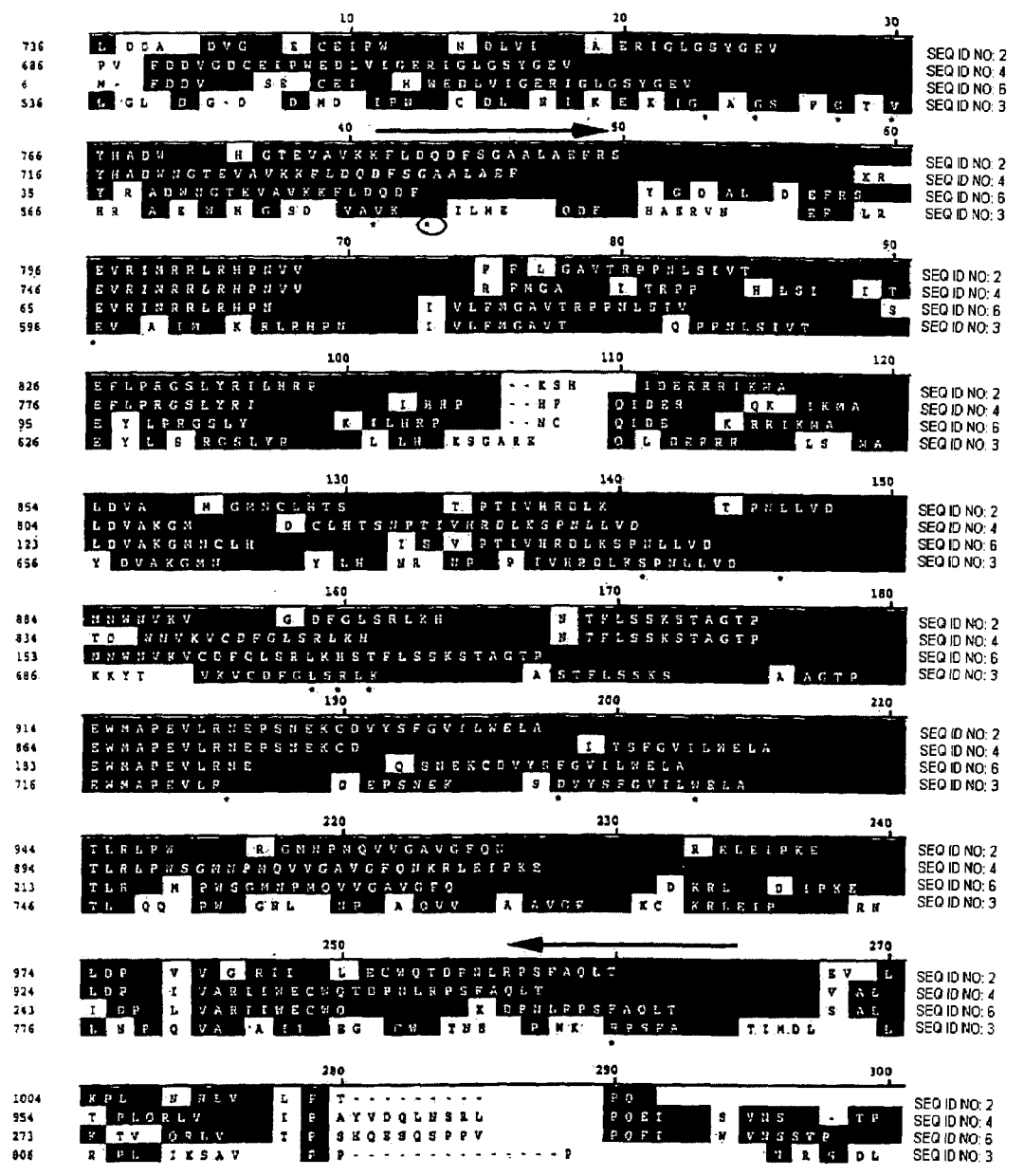

The high degree of similarity between *Arabidopsis* EDR1, TCTR2, and rice EDR1 indicates that the EDR1 gene is well conserved among both monocots and dicots, which in turn suggests that it may function in a similar manner in all flowering plants. In addition, this high degree of conservation indicates that it will be straightforward to isolate EDR1 homologs from any plant species by homology-based approaches. For example, PCR-primers derived from regions that are identical in *Arabidopsis*, tomato and rice, but that differ from the analogous region of CTR1, should amplify EDR1 homologs from most flowering plant species. Two such regions are indicated in FIG. 4 (SEQ ID NOS: 7 and 8). Degenerate primers corresponding to these regions were used to successfully amplify an EDR1 homolog from barley (SEQ ID NO:9).

The present invention is not limited to the embodiments described and exemplified above, but is capable of variation and modification without departure from the scope of the appended claims.

We claim:

1. An isolated nucleic acid molecule comprising a nucleotide sequence encoding a polypeptide sequence selected from the group consisting of SEQ ID NO: 2, SEQ ID NO: 6, and SEQ ID NO: 10.

2. The nucleic acid molecule of claim 1, wherein the nucleotide sequence encodes SEQ ID NO: 2.

3. The nucleic acid molecule of claim 2 wherein the nucleotide sequence is SEQ ID NO: 1.

4. A vector comprising the nucleic acid molecule of claim 1.

5. An isolated nucleic acid molecule comprising a nucleotide sequence selected from the group consisting of:
   a) the nucleotide sequence of SEQ ID NO: 1;
   b) a nucleotide sequence encoding SEQ ID NO: 2;
   c) a nucleotide sequence encoding SEQ ID NO: 6;
   d) a nucleotide sequence encoding SEQ ID NO: 10
   e) the nucleotide sequence of SEQ ID NO: 5; and
   f) the nucleotide sequence of SEQ ID NO: 9.

6. A vector comprising the nucleic acid molecule of claim 5.

* * * * *

SEQUENCE LISTING

```
<160> NUMBER OF SEQ ID NOS: 10

<210> SEQ ID NO 1
<211> LENGTH: 3081
<212> TYPE: DNA
<213> ORGANISM: Arabidopsis thaliana

<400> SEQUENCE: 1
ccactttttt gattgaccaa aggaagaaga agaagaagaa gaagaatctg aagagagcga      60
tgaagcatat tttcaagaag ctacacagag gtgggaatca agagcagcag aatcgaacca     120
acgatgcagc tcctccatcg gatcaaaatc ggattcacgt ttctgctaat cctcctcaag     180
caaccccttc gtcagtcact gagacgcttc cggtggccgg agctacttct tctatggcct     240
ctcctgctcc aaccgctgct tcgaaccgtg cggattacat gtcttctgag gaggagtatc     300
aagtgcagtt agccctagcg atcagtgctt cgaattcgca gtccagtgag gatccggaga     360
agcatcagat ccgagcggcg acgcttctga gcttaggaag ccatcaacgg atggattcaa     420
ggagggattc atcggaggtg gtagcccaga ggttatcgag acagtactgg gaatatggcg     480
```

```
tgcttgacta tgaggagaaa gttgtcgata gtttctacga cgtatacagt ctatccacag    540
actccgcaaa gcaggagaa atgccatcgc tggaagatct tgaaagcaat catggcacac     600
ctggctttga agctgtagtt gtaaatcgac ctattgattc ttccctgcat gagttgctag    660
aaatcgcaga gtgtattgca ctgggttgtt ctactaccag tgttagtgtg ttggtacaga    720
ggctggctga gcttgtcacc gagcatatgg gtggatctgc ggaagattcc agtatagtat    780
tggcaaggtg gactgaaaaa agcagcgagt tcaaggcagc attgaatact tgcgtattcc    840
ctattggatt tgtaaagatt ggtatctcaa ggcatcgtgc tctgcttttc aaggttttgg    900
cagatagtgt caggttacct tgtaggttgg taaaaggtag ccactacaca ggcaatgagg    960
atgatgctgt gaacacgata agactggaag atgaaagaga gtacttggtt gatcttatga   1020
cagatcctgg gacgcttata cccgctgatt ttgcaagtgc tagtaataac accgttgagc   1080
catgtaactc aaatgaaac aaatttccta cagctcagtt ttcaaatgac gtgccaaagc    1140
tctcagaagg tgaaggaagt agtcacagtt ctatggccaa ctatagttct tctttggata   1200
gaaggacaga ggctgaaagg acagattctt cataccaaa ggtgggacca cttcggaaca    1260
tagactatag ttctccttct agcgtaacta gttctactca gttggagaac aattcctcaa   1320
cagcaattgg aaaggggagt cgaggagcca taattgaatg ttcaagaaca acatgaata    1380 tagttcctta caatcagaac agtgaggaag acccaaaaaa ccttttcgca gaccttaatc   1440
catttcaaaa taagggagct gacaagctgt atatgcccac taaatcaggt ttgaataacg   1500
ttgatgattt tcatcaacag aaaaataatc ctctggttgg tagatcacct gcgccaatga   1560
tgtggaagaa ttacagttgc aatgaagccc caaagagaaa ggagaatagt tatatagaaa   1620
atcttctccc gaaactccac cgtgatcctc gttatgaaa cactcaatcc tcatatgcta    1680
cctcaagctc caatggagct atttcctcaa atgtgcatgg cagagacaat gtgacatttg   1740
tgtcaccggt tgctgtacca tcatccttca catccactga aaatcagttt agaccaagta   1800
tagtggagga tatgaacaga acaccaaca atgaactaga tcttcagcct catactgctg    1860
ctgtggtaca tggacaacag aatgatgaat ctcacatcca tgatcacaga agtacacaa    1920 gtgatgacat atccactggc tgtgatccga ggcttaagga tcacgaaagt acaagttcat   1980
ctcttgattc tacatcctac cggaatgatc ctcaagttct tgatgatgca gatgttggtg   2040
aatgtgaaat tccttggaat gatctcgtta ttgcggagag aataggatta gggtcctatg   2100
gagaggtcta tcatgctgac tggcatggca cggaagttgc tgtcaagaaa tttttggacc   2160
aggacttctc aggtgctgct ttagccgagt tcagaagcga agtacggatt atgcgaagat   2220
tgcgtcatcc aaatgttgta ttcttccttg gggctgttac tcgtcctcca aatctttcca   2280
tcgtcacaga gtttctgcct agaggaagct tgtatcgaat ccttcatcgg cccaaatctc   2340
acattgacga gcggcgccgg attaaaatgg cccttgacgt ggcaatgggg atgaactgct   2400
tacacaccag tacaccgaca attgttcatc gtgatctcaa acaccaaac cttttggttg    2460 ataacaactg gaatgttaag gtcggtgatt ttgggttgtc tcgcttaaag cacaatactt   2520
ttttatcctc caaatcaact gctggaacgc ctgaatggat ggctccagaa gttctacgca   2580
atgagccctc aaatgaaaag tgtgatgtgt acagtttcgg ggtaatactt tgggaactag   2640
caacattgag attaccatgg agaggaatga acccaatgca gtagttgga gcagttgggt    2700 tccagaatcg gcggcttgag atccccaagg aacttgatcc tgtggtggga aggatcatcc   2760
tggaatgttg gcaaacggat ccgaatctgc ggccgtcatt tgctcagctg acggaagtgc   2820
```

-continued

```
tgaagccttt gaaccggctt gtacttccta caccacaata gatgtcatct gtgtgaatat    2880
gtgaaagaaa atttggttaa tgtatactat ttgacctctg gtgctgcgca gagttattat    2940
acataagcca gcctagaatt gaggaatgta aatgaaatca atgtacacta tactacgttt    3000
tgatgtatta tttgttatag gaaaagccgc tatgctgtgc ttattttatc agaaataatg    3060
ctaataagtt aaacgtctgt c                                              3081
```

<210> SEQ ID NO 2
<211> LENGTH: 933
<212> TYPE: PRT
<213> ORGANISM: Arabidopsis thaliana

<400> SEQUENCE: 2

```
Met Lys His Ile Phe Lys Lys Leu His Arg Gly Gly Asn Gln Glu Gln
1               5                   10                  15

Gln Asn Arg Thr Asn Asp Ala Ala Pro Pro Ser Asp Gln Asn Arg Ile
            20                  25                  30

His Val Ser Ala Asn Pro Pro Gln Ala Thr Pro Ser Ser Val Thr Glu
        35                  40                  45

Thr Leu Pro Val Ala Gly Ala Thr Ser Ser Met Ala Ser Pro Ala Pro
    50                  55                  60

Thr Ala Ala Ser Asn Arg Ala Asp Tyr Met Ser Ser Glu Glu Glu Tyr
65                  70                  75                  80

Gln Val Gln Leu Ala Leu Ala Ile Ser Ala Ser Asn Ser Gln Ser Ser
                85                  90                  95

Glu Asp Pro Glu Leu His Gln Ile Arg Ala Ala Thr Leu Leu Ser Leu
            100                 105                 110

Gly Ser His Gln Arg Met Asp Ser Arg Arg Asp Ser Ser Glu Val Val
        115                 120                 125

Ala Gln Arg Leu Ser Arg Gln Tyr Trp Glu Tyr Gly Val Leu Asn Tyr
    130                 135                 140

Glu Glu Lys Val Val Asp Ser Phe Tyr Asp Val Tyr Ser Leu Ser Thr
145                 150                 155                 160

Asp Ser Ala Lys Gln Gly Glu Met Pro Ser Leu Glu Asp Leu Glu Ser
                165                 170                 175

Asn His Gly Thr Pro Gly Phe Glu Ala Val Val Asn Arg Pro Ile
            180                 185                 190

Asp Ser Ser Leu His Glu Leu Leu Glu Ile Ala Glu Cys Ile Ala Leu
        195                 200                 205

Gly Cys Ser Thr Thr Ser Val Ser Val Leu Val Gly Arg Leu Ala Glu
    210                 215                 220

Leu Val Thr Glu His Met Gly Gly Ser Ala Glu Asp Ser Ser Ile Val
225                 230                 235                 240

Leu Ala Arg Trp Thr Glu Lys Ser Ser Glu Phe Lys Ala Ala Leu Asn
                245                 250                 255

Thr Cys Val Phe Pro Ile Gly Phe Val Lys Ile Gly Ile Ser Arg His
            260                 265                 270

Arg Ala Leu Leu Phe Lys Val Leu Ala Asp Ser Val Arg Leu Pro Cys
        275                 280                 285

Arg Leu Val Lys Gly Ser His Tyr Thr Gly Asn Glu Asp Asp Ala Val
    290                 295                 300

Asn Thr Ile Arg Leu Glu Asp Glu Arg Glu Tyr Leu Val Asp Leu Met
305                 310                 315                 320

Thr Asp Pro Gly Thr Leu Ile Pro Ala Asp Phe Ala Ser Ala Ser Asn
```

```
                    325                 330                 335
Asn Thr Val Glu Pro Cys Asn Ser Asn Gly Asn Lys Phe Pro Thr Ala
                340                 345                 350
Gln Phe Ser Asn Asp Val Pro Lys Leu Ser Glu Gly Glu Gly Ser Ser
            355                 360                 365
His Ser Ser Met Ala Asn Tyr Ser Ser Ser Leu Asp Arg Arg Thr Glu
        370                 375                 380
Ala Glu Arg Thr Asp Ser Val Tyr Pro Lys Val Gly Pro Leu Arg Asn
385                 390                 395                 400
Ile Asp Tyr Ser Ser Ile Ser Ser Val Thr Ser Ser Thr Gln Leu Glu
                405                 410                 415
Asp Asp Ser Ser Thr Ala Ile Gly Lys Gly Ser Arg Gly Ala Ile Ile
                420                 425                 430
Glu Cys Ser Arg Thr Asn Met Asn Ile Val Pro Tyr Asn Gln Asn Ser
            435                 440                 445
Glu Glu Asp Pro Lys Asn Leu Phe Ala Asp Leu Asn Pro Phe Gln Asn
        450                 455                 460
Lys Gly Ala Asp Lys Leu Tyr Met Pro Thr Lys Ser Gly Leu Asn Asn
465                 470                 475                 480
Val Asp Asp Phe His Gln Gln Lys Asn Asn Pro Leu Val Gly Arg Ser
                485                 490                 495
Pro Ala Pro Met Met Trp Lys Asn Tyr Ser Cys Asn Glu Ala Pro Lys
                500                 505                 510
Arg Lys Glu Asn Ser Tyr Ile Glu Asn Leu Leu Pro Lys Leu His Arg
            515                 520                 525
Asp Pro Arg Tyr Gly Asn Thr Gln Ser Ser Tyr Ala Thr Ser Ser Ser
        530                 535                 540
Asn Gly Ala Ile Ser Ser Asn Val His Gly Arg Asp Asn Val Thr Phe
545                 550                 555                 560
Val Ser Pro Val Ala Val Pro Ser Ser Phe Thr Ser Thr Glu Asn Gln
                565                 570                 575
Phe Arg Pro Ser Ile Val Glu Asp Met Asn Arg Asn Thr Asn Asn Glu
                580                 585                 590
Leu Asp Leu Gln Pro His Thr Ala Ala Val His Gly Gln Gln Asn
            595                 600                 605
Asp Glu Ser His Ile His Asp His Arg Lys Tyr Thr Ser Asp Asp Ile
        610                 615                 620
Ser Thr Gly Cys Asp Pro Arg Leu Lys Asp His Glu Ser Thr Ser Ser
625                 630                 635                 640
Ser Leu Asp Ser Thr Ser Thr Arg Asn Asp Pro Gln Val Leu Asp Asp
                645                 650                 655
Ala Asp Val Gly Glu Cys Glu Ile Pro Ile Asn Asp Leu Val Ile Ala
                660                 665                 670
Glu Arg Ile Gly Leu Gly Ser Tyr Gly Glu Val Tyr His Ala Asp Trp
            675                 680                 685
His Gly Thr Glu Val Ala Val Leu Leu Phe Leu Asp Gln Asp Phe Ser
        690                 695                 700
Gly Ala Ala Leu Ala Glu Pro Arg Ser Glu Val Arg Ile Met Arg Arg
705                 710                 715                 720
Leu Arg His Pro Asn Val Val Phe Phe Leu Gly Ala Val Thr Arg Pro
                725                 730                 735
Pro Asn Leu Ser Ile Val Thr Glu Phe Leu Pro Arg Gly Ser Leu Thr
                740                 745                 750
```

-continued

```
Arg Ile Leu His Arg Pro Leu Ser His Ile Asp Glu Arg Arg Ile
        755                 760                 765
Leu Met Ala Leu Asp Val Ala Met Gly Met Asn Cys Leu His Thr Ser
        770                 775                 780
Thr Pro Thr Ile Val His Arg Asp Leu Lys Thr Pro Asn Leu Leu Val
785                 790                 795                 800
Asp Asn Asn Thr Asn Val Leu Val Gly Asp Phe Gly Leu Ser Arg Leu
                805                 810                 815
Lys His Asn Thr Phe Leu Ser Ser Leu Ser Thr Ala Gly Thr Pro Glu
                820                 825                 830
Thr Met Ala Pro Glu Val Leu Arg Asn Glu Pro Ser Asn Glu Leu Cys
        835                 840                 845
Asp Val Thr Ser Phe Gly Val Ile Leu Thr Glu Leu Ala Thr Leu Arg
        850                 855                 860
Leu Pro Thr Arg Gly Met Asn Pro Met Gln Val Val Gly Ala Val Gly
865                 870                 875                 880
Phe Gln Asn Arg Arg Leu Glu Ile Pro Lys Glu Leu Asp Pro Val Val
                885                 890                 895
Gly Arg Ile Ile Leu Glu Cys Thr Gln Thr Asp Pro Asn Leu Arg Pro
                900                 905                 910
Ser Phe Ala Gln Leu Thr Glu Val Leu Lys Pro Leu Asn Arg Leu Val
                915                 920                 925
Leu Pro Thr Pro Gln
        930

<210> SEQ ID NO 3
<211> LENGTH: 821
<212> TYPE: PRT
<213> ORGANISM: Arabidopsis thaliana

<400> SEQUENCE: 3

Met Glu Met Pro Gln Arg Arg Ser Asn Tyr Thr Leu Leu Ser Gln Ser
1               5                   10                  15
Asp Asp Gln Val Ser Val Ser Val Thr Gly Ala Pro Pro His Phe
            20                  25                  30
Tyr Asp Ser Leu Ser Ser Glu Asn Arg Ser Asn His Asn Ser Gly Asn
            35                  40                  45
Thr Gly Lys Ala Lys Ala Glu Arg Gly Gly Phe Asp Thr Asp Pro Ser
        50                  55                  60
Gly Gly Gly Gly Gly Asp His Arg Leu Asn Asn Gly Pro Asn Arg Val
65                  70                  75                  80
Gly Asn Asn Met Tyr Ala Ser Ser Leu Gly Leu Gln Arg Gln Ser Ser
                85                  90                  95
Gly Ser Ser Phe Gly Glu Ser Ser Leu Ser Gly Asp Tyr Tyr Met Pro
            100                 105                 110
Thr Leu Ser Ala Ala Ala Asn Glu Ile Glu Ser Val Gly Phe Pro Gln
            115                 120                 125
Asp Asp Gly Phe Arg Leu Gly Phe Gly Gly Gly Gly Asp Leu Arg
        130                 135                 140
Ile Gln Met Ala Ala Asp Ser Ala Gly Gly Ser Ser Ser Gly Lys Ser
145                 150                 155                 160
Trp Ala Gln Gln Thr Glu Glu Ser Tyr Gln Leu Gln Leu Ala Leu Ala
                165                 170                 175
Leu Arg Leu Ser Ser Glu Ala Thr Cys Ala Asp Asp Pro Asn Phe Leu
```

-continued

```
                180                 185                 190
Asp Pro Val Pro Asp Glu Ser Ala Leu Arg Thr Ser Pro Ser Ser Ala
            195                 200                 205

Glu Thr Val Ser His Arg Phe Trp Val Asn Gly Cys Leu Ser Tyr Tyr
210                 215                 220

Asp Lys Val Pro Asp Gly Phe Tyr Met Met Asn Gly Leu Asp Pro Tyr
225                 230                 235                 240

Ile Trp Thr Leu Cys Ile Asp Leu His Glu Ser Gly Arg Ile Pro Ser
                245                 250                 255

Ile Glu Ser Leu Arg Ala Val Asp Ser Gly Val Asp Ser Ser Leu Glu
            260                 265                 270

Ala Ile Ile Val Asp Arg Arg Ser Asp Pro Ala Phe Lys Glu Leu His
            275                 280                 285

Asn Arg Val His Asp Ile Ser Cys Ser Cys Ile Thr Thr Lys Glu Val
            290                 295                 300

Val Asp Gln Leu Ala Lys Leu Ile Cys Asn Arg Met Gly Gly Pro Val
305                 310                 315                 320

Ile Met Gly Glu Asp Glu Leu Val Pro Met Trp Lys Glu Cys Ile Asp
                325                 330                 335

Gly Leu Lys Glu Ile Phe Lys Val Val Pro Ile Gly Ser Leu Ser
            340                 345                 350

Val Gly Leu Cys Arg His Arg Ala Leu Leu Phe Lys Val Leu Ala Asp
            355                 360                 365

Ile Ile Asp Leu Pro Cys Arg Ile Ala Lys Gly Cys Lys Tyr Cys Asn
            370                 375                 380

Arg Asp Asp Ala Ala Ser Cys Leu Val Arg Phe Gly Leu Asp Arg Glu
385                 390                 395                 400

Tyr Leu Val Asp Leu Val Gly Lys Pro Gly His Leu Trp Glu Pro Asp
                405                 410                 415

Ser Leu Leu Asn Gly Pro Ser Ser Ile Ser Ser Pro Leu Arg
            420                 425                 430

Phe Pro Arg Pro Lys Pro Val Glu Pro Ala Val Asp Phe Arg Leu Leu
            435                 440                 445

Ala Lys Gln Tyr Phe Ser Asp Ser Gln Ser Leu Asn Leu Val Phe Asp
450                 455                 460

Pro Ala Ser Asp Asp Met Gly Phe Ser Met Phe His Arg Gln Tyr Asp
465                 470                 475                 480

Asn Pro Gly Gly Glu Asn Asp Ala Leu Ala Glu Asn Gly Gly Gly Ser
                485                 490                 495

Leu Pro Pro Ser Ala Asn Met Pro Pro Gln Asn Met Met Arg Ala Ser
            500                 505                 510

Asn Gln Ile Glu Ala Ala Pro Met Asn Ala Pro Pro Ile Ser Gln Pro
            515                 520                 525

Val Pro Asn Arg Ala Asn Arg Glu Leu Gly Leu Asp Gly Asp Asp Met
            530                 535                 540

Asp Ile Pro Trp Cys Asp Leu Asn Ile Lys Glu Lys Ile Gly Ala Gly
545                 550                 555                 560

Ser Phe Gly Thr Val His Arg Ala Glu Trp His Gly Ser Asp Val Ala
                565                 570                 575

Val Lys Ile Leu Met Glu Asn Asp Phe His Ala Glu Arg Val Asn Glu
            580                 585                 590

Phe Leu Arg Glu Val Ala Ile Met Lys Arg Leu Arg His Pro Asn Ile
            595                 600                 605
```

```
Val Leu Phe Met Gly Ala Val Thr Gly Pro Thr Glu Tyr Leu Ser Arg
    610                 615                 620

Gly Ser Leu Tyr Arg Leu Leu His Lys Ser Pro Asn Leu Ser Ile Val
625                 630                 635                 640

Gly Ala Arg Glu Asn Leu Asp Glu Arg Arg Leu Ser Met Ala Tyr
                645                 650                 655

Asp Val Ala Lys Gly Met Asn Tyr Leu His Asn Arg Asn Pro Pro Ile
                660                 665                 670

Val His Arg Asp Leu Lys Ser Pro Asn Leu Leu Val Asp Lys Lys Tyr
                675                 680                 685

Thr Val Lys Val Cys Asp Phe Gly Leu Ser Arg Leu Lys Ala Ser Thr
                690                 695                 700

Phe Leu Ser Ser Lys Ser Ala Ala Gly Thr Pro Glu Trp Met Ala Pro
705                 710                 715                 720

Glu Val Leu Arg Asp Glu Pro Ser Asn Glu Lys Ser Asp Val Tyr Ser
                725                 730                 735

Phe Gly Val Ile Leu Trp Glu Leu Ala Thr Leu Gln Gln Pro Trp Gly
                740                 745                 750

Asn Leu Asn Pro Ala Gln Val Ala Ala Val Gly Phe Lys Cys Lys
            755                 760                 765

Arg Leu Glu Ile Pro Arg Asn Leu Asn Pro Gln Val Ala Ala Ile Ile
    770                 775                 780

Glu Gly Cys Trp Thr Asn Glu Pro Trp Lys Arg Pro Ser Phe Ala Thr
785                 790                 795                 800

Ile Met Asp Leu Leu Arg Pro Leu Ile Lys Ser Ala Val Pro Pro Pro
                805                 810                 815

Asn Arg Ser Asp Leu
            820

<210> SEQ ID NO 4
<211> LENGTH: 982
<212> TYPE: PRT
<213> ORGANISM: Lycopersicon esculentum

<400> SEQUENCE: 4

Met Lys His Ile Phe Lys Lys Leu His His Ser Asn Arg Ser Asn Asp
1               5                   10                  15

Ala Asn Ser Thr Ser Ser Ile Ser Ser Ser Ser Pro Ala Ser Ser
            20                  25                  30

Leu Ser Ser Ala Ser Cys Thr Thr Asp His Arg Asn Ser Asn Ser Val
        35                  40                  45

Ser Gly Ser Pro Leu Ser Pro Ser Thr Ile Ser Thr Ala Ser Thr Thr
    50                  55                  60

Thr Thr Pro Ala Ala Pro Val Gly Ala Gly Gly Gly Gly Gly Gly
65                  70                  75                  80

Asn Leu Ser Thr Ile Asn Arg Gln Gln Asp Tyr Tyr Thr Ser Glu Glu
                85                  90                  95

Glu Tyr Gln Val Gln Leu Ala Leu Leu Ser Val Ser Ser Gln
            100                 105                 110

Ser Gln Asp Pro Phe Pro Ser Asp Asx Gly Arg Thr Ala Val Asp Leu
        115                 120                 125

Ala Arg Asp Arg Glu Asp Ala Ala Ala Asp Leu Leu Ser Arg Gln Tyr
    130                 135                 140

Trp Asp Tyr Gly Val Met Asp Tyr Val Asn Ser Ser Asn Gly His Gly
```

-continued

```
            145                 150                 155                 160
Glu Glu Lys Val Val Asp Gly Phe Tyr Asp Val Tyr Asn Leu Phe Thr
                165                 170                 175
Asp Pro Ala Ser Arg Gly Lys Met Pro Ser Leu Ser Asn Pro Gly Thr
            180                 185                 190
Ser Asn Phe Glu Gly Val Ile Ile Asn Gln Arg Ile Asp Pro Ser Leu
            195                 200                 205
Glu Glu Leu Met Gln Ile Ala His Cys Ile Thr Leu Glu Leu Glu Thr
            210                 215                 220
Asp Cys Pro Ala Ser Glu Ile Ser Leu Leu Val Leu Arg Leu Ser Glu
225                 230                 235                 240
Leu Val Thr Gly His Leu Gly Gly Pro Val Lys Asp Ala Asn Ile Ile
                245                 250                 255
Leu Ala Lys Trp Met Glu Ile Ser Thr Glu Leu Arg Thr Ser Leu His
                260                 265                 270
Thr Ser Val Leu Pro Ile Gly Ser Leu Lys Ile Gly Leu Ser Arg His
                275                 280                 285
Arg Ala Leu Leu Phe Lys Val Leu Ala Asp His Val Gly Ile Pro Cys
            290                 295                 300
Arg Leu Val Lys Gly Ser His Tyr Thr Gly Val Glu Asp Asp Ala Val
305                 310                 315                 320
Asn Ile Val Lys Leu Pro Asn Asp Ser Glu Phe Leu Val Asp Leu Met
                325                 330                 335
Gly Ala Pro Gly Thr Leu Ile Pro Ala Asp Val Leu Ser Ala Lys Asp
                340                 345                 350
Ala Ser Phe Asn Ser Pro Lys Leu Asn Lys Ile Pro Ser Leu Pro Ser
            355                 360                 365
Asn Ser His Ser Gly Val Ser Tyr Pro Arg Arg Asn Leu Leu Ser Gly
            370                 375                 380
Gln Asn Ser Val Leu Gly Asp Asp Phe Ser Gly Arg Ser Lys Pro Glu
385                 390                 395                 400
Lys Ile Glu Ser Val His Ser Ile Ser Asp Ala Gly Gly Ser Ser Thr
                405                 410                 415
Ala Gly Ser Ser Gly Ile Asn Lys Arg Pro Ser Ser Asn Gly Val Asp
            420                 425                 430
Trp Thr Ser Pro Leu Ala Ile Gly Thr Ser Leu Tyr Lys Gly Gly Arg
            435                 440                 445
Gly Pro Asn Ala Ala Gly Asp Gly Leu Arg Leu Asn Val Asn Val Val
            450                 455                 460
Pro Tyr Asp Gln Asn Asn Pro Glu Asp Pro Lys Asn Leu Phe Ala Asp
465                 470                 475                 480
Leu Asn Pro Phe Gln Ile Lys Gly Ser Gly Asn Thr Leu Leu Gln Lys
                485                 490                 495
Asn Pro Ala Arg Asn Lys Val Ser Glu Leu Gln Gln Pro Ile Asn Thr
            500                 505                 510
Leu Ile Pro Gly Arg Pro Pro Ala Pro Met Met Trp Lys Asn Arg Tyr
            515                 520                 525
Ala Pro Asn Glu Val Pro Arg Lys Asn Glu Ser Asp Ser Glu Gly Leu
            530                 535                 540
Phe Pro Lys Lys Asn Gly Gly Ser Ser Gly Tyr Asn Ile Ser Ser Ile
545                 550                 555                 560
Ala Ser Thr Ser Ser Asn Ile Pro Gln Lys Ser Ser Thr Asp Thr Ser
                565                 570                 575
```

```
Arg Leu His Gly Asn Ser Arg Pro Ala Tyr Arg Gly Asn Asp Glu Val
            580                 585                 590

Ala Ser Thr Arg Asn Asn Ser Ser Ile Leu Ser Ala Glu Leu Glu Phe
        595                 600                 605

Arg Arg Leu Ser Val Gln Asn Ser Gln Asn Asn Arg Glu Thr Ser
        610                 615                 620

Gln Trp Glu Gly His Ser Leu Gln Ser Asp Asp Leu Asn Arg Thr Gln
625                 630                 635                 640

Ala Tyr Gly Asp Asp Ile Ile Val Glu Ser Asp His Thr Arg Asn Leu
            645                 650                 655

Gln Ala Gln Ser Ile Gly Thr Asn Ile Lys Leu Lys Glu Pro Glu Asn
            660                 665                 670

Pro Thr Ser Ser Gly Asn Leu Gly Pro Ser Gln Val Asp Pro Val Phe
            675                 680                 685

Asp Asp Val Gly Asp Cys Glu Ile Pro Trp Glu Asp Leu Val Ile Gly
            690                 695                 700

Glu Arg Ile Gly Leu Gly Ser Tyr Gly Glu Val Tyr His Ala Asp Trp
705                 710                 715                 720

Asn Gly Thr Glu Val Ala Val Lys Lys Phe Leu Asp Gln Asp Phe Ser
            725                 730                 735

Gly Ala Ala Leu Ala Glu Phe Lys Arg Glu Val Arg Ile Met Arg Arg
            740                 745                 750

Lys Arg His Pro Asn Val Val Arg Phe Met Gly Ala Ile Thr Arg Pro
            755                 760                 765

Pro His Leu Ser Ile Ile Thr Glu Phe Leu Pro Arg Gly Ser Leu Tyr
            770                 775                 780

Arg Ile Ile His Arg Pro His Phe Gln Ile Asp Glu Arg Gln Lys Ile
785                 790                 795                 800

Lys Met Ala Leu Asp Val Ala Lys Gly Met Asp Cys Leu His Thr Ser
            805                 810                 815

Asn Pro Thr Ile Val His Arg Asp Leu Lys Ser Pro Asn Leu Leu Val
            820                 825                 830

Asp Thr Asp Trp Asn Val Lys Val Cys Asp Phe Gly Leu Ser Arg Leu
        835                 840                 845

Lys His Asn Thr Phe Leu Ser Ser Lys Ser Thr Ala Gly Thr Pro Glu
    850                 855                 860

Trp Met Ala Pro Glu Val Leu Arg Asn Glu Pro Ser Asn Glu Lys Cys
865                 870                 875                 880

Asp Ile Tyr Ser Phe Gly Val Ile Leu Trp Glu Leu Ala Thr Leu Arg
            885                 890                 895

Leu Pro Trp Ser Gly Met Asn Pro Met Gln Val Val Gly Ala Val Gly
            900                 905                 910

Phe Gln Asn Lys Arg Leu Glu Ile Pro Lys Glu Leu Asp Pro Ile Val
        915                 920                 925

Ala Arg Ile Ile Trp Glu Cys Trp Gln Thr Asp Pro Asn Leu Arg Pro
        930                 935                 940

Ser Phe Ala Gln Leu Thr Val Ala Leu Thr Pro Leu Gln Arg Leu Val
945                 950                 955                 960

Ile Pro Ala Tyr Val Asp Gln Leu Asn Ser Arg Leu Pro Gln Glu Ile
            965                 970                 975

Ser Val Asn Ser Thr Pro
            980
```

-continued

<210> SEQ ID NO 5
<211> LENGTH: 3160
<212> TYPE: DNA
<213> ORGANISM: Oryza sativa

<400> SEQUENCE: 5

| | | | | | |
|---|---|---|---|---|---|
| agcagatcag | gaaggccaag | ctgataagcc | tcggcagggg | caaccgcttc | gccgccgtcc | 60 |
| gggacgacga | gcaaaccgcg | gatgcgctct | cccgccgcta | ccgggactac | aactttcttg | 120 |
| attaccatga | gaaagttatt | gatggcttct | atgacatttt | tggcccctct | atggaatcat | 180 |
| caaagcaagg | gaagatgcca | tcactagcag | atcttcaaac | gggcataggc | gacctgggtt | 240 |
| ttgaagtcat | cgtaatcaat | cgtgccattg | ataccacctt | acaggagatg | gaacaagttg | 300 |
| cacaatgtat | cctgcttgac | tttcctgttg | caaatattgc | agccttagtt | caagaaatag | 360 |
| ccgagcttgt | tacagatcac | atgggtggac | ctgtgaaaga | tgcaaatgac | atgctcacta | 420 |
| gatggctaga | gaaaagcact | gagctaagaa | cctcactaca | cacaagtttg | ttgcctattg | 480 |
| gctgcatcaa | gataggtctg | tctcgtcacc | gtgccctact | tttcaagatt | ctcgctgata | 540 |
| gtgttggcat | tccttgcaag | cttgtcaaag | ggagtaatta | tactggtgat | gatgatgatg | 600 |
| ctatcaacat | aataaagatg | aatgaaaggg | agttttggt | tgatctcatg | gctgctcccg | 660 |
| gtactcttat | tccatcagat | gtcttaagtt | ggaagggcaa | ctcattaaat | tctaatgcaa | 720 |
| gactcaccca | gaatccattg | gctgggtcat | caagtacaac | tgattctaat | ctcagtgcca | 780 |
| atgcattacc | acccggacat | aaaggtggcc | aactgccttt | atttagcagt | ggcgattgga | 840 |
| tattggccag | tcaatctgga | tatgaaaaag | atggagccac | cacatcttca | caggcctctt | 900 |
| caagtggcac | aacatctgtt | gctgctggaa | gcgcttttga | tagttcttgg | acattagttt | 960 |
| ctcatggaca | atcagatgat | ccatcaacct | ctgctggtat | gtcagcacag | cagaaagtta | 1020 |
| tacttccagg | tggagaacat | ccatggaatg | agaatataaa | tgcgcgaaat | gagaatataa | 1080 |
| aacttgtttc | agatttacaa | gggaattcag | agtccatcaa | cttatttgcc | gaccttaatc | 1140 |
| cttttggggg | tagggagccc | aaaaggactt | cagtgccatt | aaatgggcca | gataatagaa | 1200 |
| ataatgagtt | gcaaagacgc | agagagaatg | tagtccctag | cacacgaaga | ccccagcagc | 1260 |
| gattagttat | gaaaaactgg | tctccttaca | atgatgtttc | caacaacaag | cagtacaatt | 1320 |
| atgttgagga | ttcatttgca | cgtagaaata | ttggtgataa | tgctgcatca | tcatctcagg | 1380 |
| tggcacggcc | atctgcaaaa | aatactaatc | ttaatgttgg | agtgcgcact | gatacaccat | 1440 |
| acatggcagc | tcataattat | gataatagta | tggctggttc | ctctgcaatg | aagatgactt | 1500 |
| ctacagctgg | gattgggaag | gttcctgata | aggttctgta | cggtgatttg | gacaagggcc | 1560 |
| ttactaattc | tagactgggg | gatcaaccac | cgatagaaag | acataaatgg | ggcaattctg | 1620 |
| tagaaggaag | gattccaaca | ggcacagttc | acaatcaagc | aaaagaacac | aaggagaact | 1680 |
| tcgatggaaa | gcaagacaat | aagaagttac | atcctgatcc | aaagaaatcc | ccacttgaca | 1740 |
| gattcatgga | cacatcaatg | ccatcaagga | accctgaatc | cgtttcacca | tcctttgcta | 1800 |
| ggtcacacaa | gctagacacc | atgttcgacg | atgtgtctga | atgtgaaatt | cattgggaag | 1860 |
| atcttgtgat | tggtgaaagg | attggcttag | gttcatatgg | agaggtgtac | cgtgctgatt | 1920 |
| ggaatggaac | agaagtagct | gtcaagaaat | tcttggatca | agatttctat | ggtgatgctt | 1980 |
| tggatgaatt | ccggagtgaa | gtgcggatta | tgcgtcgact | gcgtcatcca | aatattgttc | 2040 |
| tcttcatggg | tgctgttact | cgtcctccaa | acttatctat | tgtatctgag | tatcttccaa | 2100 |
| ggggaagctt | atataagatc | cttcaccgtc | ctaattgcca | aattgacgag | aagcgtagaa | 2160 |

-continued

```
ttaaaatggc ccttgatgtg gccaaaggaa tgaattgcct ccatattagt gtaccaacaa    2220
ttgttcatcg ggatcttaaa tcaccaaact tgctggttga caacaactgg aatgtgaagg    2280
tttgtgattt tggactttca cgcttgaagc acagtacatt cttatcatcc aaatccactg    2340
ctggaactcc ggagtggatg gcacctgagg tcttgcggaa tgaacaatca aatgaaaagt    2400
gtgatgttta cagctttggt gtcatcttgt gggaattagc aacacttagg atgccatgga    2460
gtggaatgaa tccaatgcaa gttgttgggg cagtcggctt ccaggacaag cggctcgata    2520
ttcccaagga aattgatcct ctagttgcaa ggatcatatg ggaatgctgg cagaaggatc    2580
caaatttgcg gccctcgttt gcacagttaa ccagtgcttt gaagactgtc caaaggctag    2640
taacccctcc tcaccaggag tcccagagcc ctcctgtgcc tcaagaaata tgggtgaatt    2700
cttccacccc ttgatgttga ggggcattcc actctcaaaa ttgtgagtaa ttattgatga    2760
ttgttgctgt taagtttgtt caagtctgca aatgtgggcg cactgtagat tctagcggcc    2820
ctaatggtag acatccctgc tgccgcgaca aagaaccca gcagtagagt atgtatagag    2880
actatagtca tcgaccaaaa cgatgacccg aagaagaaat ccagtctgtg gcatctcatt    2940
tttcatgttc ccagtttgcc tttgtaaaac cttttggatt cgagccctct ggaaagcagt    3000
gagagctcgt ggcgttggat taagaaggat ctgtgtctga ctgtgtttac aagtggattg    3060
gataattgtt gctgcagaac atgacatctt ggaagttaaa aatgttgtaa tatgcaattt    3120
ttttaaactt gcaattcgaa tgcagtatat gaacatgatg                          3160
```

<210> SEQ ID NO 6
<211> LENGTH: 903
<212> TYPE: PRT
<213> ORGANISM: Oryza sativa

<400> SEQUENCE: 6

```
Gln Ile Arg Lys Ala Lys Leu Ile Ser Leu Gly Arg Gly Asn Arg Phe
1               5                   10                  15

Ala Ala Val Arg Asp Asp Glu Gln Thr Ala Asp Ala Leu Ser Arg Arg
            20                  25                  30

Tyr Arg Asp Tyr Asn Phe Leu Asp Tyr His Glu Lys Val Ile Asp Gly
        35                  40                  45

Phe Tyr Asp Ile Phe Gly Pro Ser Met Glu Ser Lys Gln Gly Lys
    50                  55                  60

Met Pro Ser Leu Ala Asp Leu Gln Thr Gly Ile Gly Asp Leu Gly Phe
65                  70                  75                  80

Glu Val Ile Val Ile Asn Arg Ala Ile Asp Thr Thr Leu Gln Glu Met
                85                  90                  95

Glu Gln Val Ala Gln Cys Ile Leu Leu Asp Phe Pro Val Ala Asn Ile
            100                 105                 110

Ala Ala Leu Val Gln Arg Ile Ala Glu Leu Val Thr Asp His Met Gly
        115                 120                 125

Gly Pro Val Lys Asp Ala Asn Asp Met Leu Thr Arg Trp Leu Glu Lys
    130                 135                 140

Ser Thr Glu Leu Arg Thr Ser Leu His Thr Ser Leu Leu Pro Ile Gly
145                 150                 155                 160

Cys Ile Lys Ile Gly Leu Ser Arg His Arg Ala Leu Leu Phe Lys Ile
                165                 170                 175

Leu Ala Asp Ser Val Gly Ile Pro Cys Lys Leu Val Lys Gly Ser Asn
            180                 185                 190
```

```
Tyr Thr Gly Asp Asp Asp Ala Ile Asn Ile Ile Lys Met Asn Glu
        195                 200                 205
Arg Glu Phe Leu Val Asp Leu Met Ala Ala Pro Gly Thr Leu Ile Pro
210                 215                 220
Ser Asp Val Leu Ser Trp Lys Gly Asn Ser Leu Asn Ser Asn Ala Arg
225                 230                 235                 240
Leu Thr Gln Asn Pro Leu Ala Gly Ser Ser Thr Thr Asp Ser Asn
                245                 250                 255
Leu Ser Ala Asn Ala Leu Pro Pro Gly His Lys Gly Gly Gln Leu Pro
                260                 265                 270
Leu Phe Ser Ser Gly Asp Trp Ile Leu Ala Ser Gln Ser Gly Tyr Glu
        275                 280                 285
Lys Asp Gly Ala Thr Thr Ser Ser Gln Ala Ser Ser Gly Thr Thr
                290                 295                 300
Ser Val Ala Ala Gly Ser Ala Phe Asp Ser Ser Trp Thr Leu Val Ser
305                 310                 315                 320
His Gly Gln Ser Asp Asp Pro Ser Thr Ser Ala Gly Met Ser Ala Gln
                325                 330                 335
Gln Lys Val Ile Leu Pro Gly Gly Glu His Pro Trp Asn Glu Asn Ile
                340                 345                 350
Asn Ala Arg Asn Glu Asn Ile Lys Leu Val Ser Asp Leu Gln Gly Asn
                355                 360                 365
Ser Glu Ser Ile Asn Leu Phe Ala Asp Leu Asn Pro Phe Gly Gly Arg
        370                 375                 380
Glu Pro Lys Arg Thr Ser Val Pro Leu Asn Gly Pro Asp Asn Arg Asn
385                 390                 395                 400
Asn Glu Leu Gln Arg Arg Arg Glu Asn Val Val Pro Ser Thr Arg Arg
                405                 410                 415
Pro Gln Gln Arg Leu Val Met Lys Asn Trp Ser Pro Tyr Asn Asp Val
                420                 425                 430
Ser Asn Asn Lys Gln Tyr Asn Tyr Val Glu Asp Ser Phe Ala Arg Arg
        435                 440                 445
Asn Ile Gly Asp Asn Ala Ala Ser Ser Ser Gln Val Ala Arg Pro Ser
        450                 455                 460
Ala Lys Asn Thr Asn Leu Asn Val Gly Val Arg Thr Asp Thr Pro Tyr
465                 470                 475                 480
Met Ala Ala His Asn Tyr Asp Asn Ser Met Ala Gly Ser Ser Ala Met
                485                 490                 495
Lys Met Thr Ser Thr Ala Gly Ile Gly Lys Val Pro Asp Lys Val Leu
                500                 505                 510
Tyr Gly Asp Leu Asp Lys Gly Leu Thr Asn Ser Arg Leu Gly Asp Gln
        515                 520                 525
Pro Pro Ile Glu Arg His Lys Trp Gly Asn Ser Val Glu Gly Arg Ile
        530                 535                 540
Pro Thr Gly Thr Val His Asn Gln Ala Lys Glu His Lys Glu Asn Phe
545                 550                 555                 560
Asp Gly Lys Gln Asp Asn Lys Lys Leu His Pro Asp Pro Lys Lys Ser
                565                 570                 575
Pro Leu Asp Arg Phe Met Asp Thr Ser Met Pro Ser Arg Asn Pro Glu
        580                 585                 590
Ser Val Ser Pro Ser Phe Ala Arg Ser His Lys Leu Asp Thr Met Phe
        595                 600                 605
Asp Asp Val Ser Glu Cys Glu Ile His Trp Glu Asp Leu Val Ile Gly
```

-continued

```
               610                 615                 620
Glu Arg Ile Gly Leu Gly Ser Tyr Gly Val Tyr Arg Ala Asp Trp
625                 630                 635                 640

Asn Gly Thr Glu Val Ala Val Lys Lys Phe Leu Asp Gln Asp Phe Tyr
                645                 650                 655

Gly Asp Ala Leu Asp Glu Phe Arg Ser Glu Val Arg Ile Met Arg Arg
            660                 665                 670

Leu Arg His Pro Asn Ile Val Leu Phe Met Gly Ala Val Thr Arg Pro
        675                 680                 685

Pro Asn Leu Ser Ile Val Ser Glu Tyr Leu Pro Arg Gly Ser Leu Tyr
    690                 695                 700

Lys Ile Leu His Arg Pro Asn Cys Gln Ile Asp Glu Lys Arg Arg Ile
705                 710                 715                 720

Lys Met Ala Leu Asp Val Ala Lys Gly Met Asn Cys Leu His Ile Ser
                725                 730                 735

Val Pro Thr Ile Val His Arg Asp Leu Lys Ser Pro Asn Leu Leu Val
            740                 745                 750

Asp Asn Asn Trp Asn Val Lys Val Cys Asp Phe Gly Leu Ser Arg Leu
        755                 760                 765

Lys His Ser Thr Phe Leu Ser Ser Lys Ser Thr Ala Gly Thr Pro Glu
    770                 775                 780

Trp Met Ala Pro Glu Val Leu Arg Asn Glu Gln Ser Asn Glu Lys Cys
785                 790                 795                 800

Asp Val Tyr Ser Phe Gly Val Ile Leu Trp Glu Leu Ala Thr Leu Arg
                805                 810                 815

Met Pro Trp Ser Gly Met Asn Pro Met Gln Val Val Gly Ala Val Gly
            820                 825                 830

Phe Gln Asp Lys Arg Leu Asp Ile Pro Lys Glu Ile Asp Pro Leu Val
        835                 840                 845

Ala Arg Ile Ile Trp Glu Cys Trp Gln Lys Asp Pro Asn Leu Arg Pro
    850                 855                 860

Ser Phe Ala Gln Leu Thr Ser Ala Leu Lys Thr Val Gln Arg Leu Val
865                 870                 875                 880

Thr Pro Ser His Gln Glu Ser Gln Ser Pro Val Pro Gln Glu Ile
                885                 890                 895

Trp Val Asn Ser Ser Thr Pro
            900
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 7

```
Ala Val Lys Lys Phe Leu Asp Gln Asp
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 8

Asp Pro Asn Leu Arg Pro Ser Phe Ala
1               5

<210> SEQ ID NO 9
<211> LENGTH: 3316
<212> TYPE: DNA
<213> ORGANISM: Hordeum vulgare

<400> SEQUENCE: 9

| | | | | | |
|---|---|---|---|---|---|
| cgcatccctg | atcacatcgc | caaactgaaa | caactaagac | aggaaatctt | ttcgaaaccc | 60 |
| aaaccctagg | tgctcgcggg | gagcgccatg | aagatcccat | ttgtgaccaa | gtggtcgcac | 120 |
| cgatccagcg | agcccgcggg | gccgtcgaat | tcggctgcag | cgcagcagca | gcagccgccg | 180 |
| ccgttgtctc | catcggcgcc | atctcgttcg | cctcccgtgg | cgtcgacaga | ggcggcaggg | 240 |
| gatgagttca | ttctgcagga | ggaagagtac | cagatgcagc | tggcgttggc | gctatcagcg | 300 |
| tcggcgtcgg | gcgccgaggg | cgcggggggat | cccgacgggg | agcagattag | aaaggccaag | 360 |
| ctgatgagtc | tcgggaaggg | cgacccagtc | accaacagcg | atcttggtgg | gggatacacc | 420 |
| gcggagtcgc | tctcccgccg | ttacagggac | tataactttc | ttgattataa | tgagaaagta | 480 |
| attgatggat | tctacgacat | atttggcccc | tctgcggaat | catctgggca | cggcaaaata | 540 |
| ccatcgctgg | cagagcttca | catgagcatt | ggggatcttg | gatatgaagt | aattgtggtt | 600 |
| gactataaat | ttgataatgc | tctgcaggag | atgaaggaag | tagcagaatg | ctgcctgttg | 660 |
| ggctgtcctg | acattacagt | attggtgcga | cgaatagctg | aagttgttgc | agatcatatg | 720 |
| ggtggtccag | tgatcgatgc | aaatgaaatg | atcactaggg | ggttgagcaa | aagcattgag | 780 |
| cagaggacat | cacaccagac | aagccttctg | catattggta | gtatagagat | aggcttgtct | 840 |
| cgccatcgcg | ccttactttt | caagattctt | gctgatatgg | ttggtatccc | ttgtaagctg | 900 |
| gttaaaggga | gccactacac | tggtgttgta | gatgacgcta | ttaacataat | aaagatggat | 960 |
| aacaaaaggg | agttttttggt | ggatgttatg | gctgctccag | ggactctcat | tccagcagat | 1020 |
| gtctttaatt | caaagggtac | tccattcaac | ttcagtcaaa | cattgggtca | gaatcaggtg | 1080 |
| gtggagtcag | caagtaacat | cgaagatgac | ccagttgcat | tacagtcaga | gcatgaacat | 1140 |
| taccaagggc | atatgtttgc | caataatgat | cgggtctcag | acaatctatc | aagctatgag | 1200 |
| aatacaatga | ctgctggaag | tagtgctagt | gaacctggga | cattaggtaa | agcatcaact | 1260 |
| ttggctggtg | ctccttccaa | gcagaagaag | aatctgcagt | tgattccaga | ctctcatgaa | 1320 |
| attgacgagt | cccgaaacct | atttgcggag | tttgatcctt | tcaatgctac | tgaatctggt | 1380 |
| aaaagctcat | tggcattcaa | gggattaaac | aatagaaaca | gtgatttccg | aaggcgtaga | 1440 |
| gagaatgtag | tcccaccatc | tgcaagatct | caacagccat | tggtgmtgaa | aaactggtcc | 1500 |
| gcttgcaatg | acatttccaa | caacaagcaa | tacaatgttg | ctgatgggtc | agttcctcgg | 1560 |
| agaaatgcca | ctgacaatgc | atcgtcatct | cagttggcgt | tgtcaactgc | aaagcattac | 1620 |
| aatcccaatg | tcagagagct | aaacgataga | atgtatgctg | cacctgctcg | taattatgac | 1680 |
| aataggataa | ttggtacctc | ggctatggcc | aaagcatcga | ctggagactg | ccttgacaga | 1740 |
| tcacaggtgc | cacctggtct | ttattatgac | aagatgcttg | gtacctcttc | tatgaataca | 1800 |
| gcttcttcat | ccggaattgg | aaaagttgca | gaaaaggacc | ttcagaatga | tctgaaaaag | 1860 |
| ggtcccatct | attctaggtt | tgacggtgaa | ctttctaaaa | atgctcaagg | atttactccc | 1920 |
| gaaagggatg | aacacaagga | aaattgtggc | agttatgacc | acagaatgtt | acatcctgat | 1980 |
| ccaagaaagt | cccctcttga | cagattcatg | gacaggccaa | ggcagaacat | agaatgtgtt | 2040 |

-continued

```
tctccatccc aagttggatc aagtaaagtt gacttggtgt tggatgaagt atctgaatgc      2100
gaaatccttt gggaagatct tgtaatcgat gaaagaattg cataggttc atatggagaa       2160 gtctaccatg ctgattggaa tggaactgaa gtagctgtaa agaagttctt ggatcaagag      2220
ttctatggtg atgctttgga ggaattccgt tgtgaagtgc ggattatgcg tcggctccgt      2280
catccaaata ttgttctctt tatgggcgcg gtaacacggc ctccacactt atctattgta      2340
tcagaatatc ttccaagggg aagcttatat aagattatcc atcgccctaa ttgccaaatt     2400
gacgagaagc gtaggattaa aatggcccctt gatgtggcca gaggcatgaa ttgtcttcat    2460
accagtgtac caacaattgt tcaccgggat ctaaaatcac caaacttgct ggttgacgat     2520
aattggactg tgaaggtctg tgatttcgga cttt cacgtc tgaagcacag tacatttttg    2580
tcgtcaaaat ccactgccgg gactcctgaa tggatgcac cagaggtttt gcggaatgag      2640
caatccaatg agaagtgtga tatttacagc tttggtgtca tcttgtggga gctagcaaca    2700
ctgagaaagc catggcatgg gatgaaccaa atgcaagttg tgggcgccgt tggcttccag     2760
gatcgacggc ttgacattcc aaaagaagtt gatcctatag ttgcatcaat tatacgtgat    2820
tgttggcaga aggatccaaa cttgcgccct tctttcatcc aattaactag ctacctgaag    2880
acattgcaaa ggctagtaat ccctt cacat caggagacag cgagcaatca tgtaccctat   2940
gaaatatctt tatatcggtg aaccgcacat ctcacatctc taccccgggg ttgtcatcca    3000
ccaagtgtga ataaggagta attatgattt tgtcaccata tctgggtccc agtctagata    3060
gcattcaccc cgctgttgca agcaaaagct ctgctgcggg tatgtacagt acatataggc    3120
tgataagatg aaacagcagg aggagaaaac aataccagtt ttacgtttaa gtggaactgt    3180
ggattgtgga ctgacaggga gagcgaaatg tgtaactatg cgtcgagtta gttgcatcac    3240
agataagctg gcaatctgga acagtgcatt gtgtgtttga ttcctttctg ccatactgaa   3300
ataaaggtca cttcag                                                    3316
```

<210> SEQ ID NO 10
<211> LENGTH: 970
<212> TYPE: PRT
<213> ORGANISM: Hordeum vulgare
<220> FEATURE:
<221> NAME/KEY: misc_feature
<222> LOCATION: (467)..(467)
<223> OTHER INFORMATION: Xaa is any amino acid

<400> SEQUENCE: 10

```
Met Lys Ile Pro Phe Val Thr Lys Trp Ser His Arg Ser Glu Pro
1               5                   10                  15

Ala Gly Pro Ser Asn Ser Ala Ala Gln Gln Gln Gln Pro Pro
            20                  25                  30

Leu Ser Pro Ser Ala Pro Ser Arg Ser Pro Pro Val Ala Ser Thr Glu
        35                  40                  45

Ala Ala Gly Asp Glu Phe Ile Leu Gln Glu Glu Tyr Gln Met Gln
    50                  55                  60

Leu Ala Leu Ala Leu Ser Ala Ser Ala Ser Gly Ala Glu Gly Ala Gly
65                  70                  75                  80

Asp Pro Asp Gly Glu Gln Ile Arg Lys Ala Lys Leu Met Ser Leu Gly
                85                  90                  95

Lys Gly Asp Pro Val Thr Asn Ser Asp Leu Gly Gly Gly Tyr Thr Ala
            100                 105                 110

Glu Ser Leu Ser Arg Arg Tyr Arg Asp Tyr Asn Phe Leu Asp Tyr Asn
        115                 120                 125
```

```
Glu Lys Val Ile Asp Gly Phe Tyr Asp Ile Phe Gly Pro Ser Ala Glu
    130                 135                 140

Ser Ser Gly His Gly Lys Ile Pro Ser Leu Ala Glu Leu His Met Ser
145                 150                 155                 160

Ile Gly Asp Leu Gly Tyr Glu Val Ile Val Asp Tyr Lys Phe Asp
                165                 170                 175

Asn Ala Leu Gln Glu Met Lys Glu Val Ala Glu Cys Cys Leu Leu Gly
            180                 185                 190

Cys Pro Asp Ile Thr Val Leu Val Arg Arg Ile Ala Glu Val Val Ala
        195                 200                 205

Asp His Met Gly Gly Pro Val Ile Asp Ala Asn Glu Met Ile Thr Arg
    210                 215                 220

Trp Leu Ser Lys Ser Ile Glu Gln Arg Thr Ser His Gln Thr Ser Leu
225                 230                 235                 240

Leu His Ile Gly Ser Ile Glu Ile Gly Leu Ser Arg His Arg Ala Leu
                245                 250                 255

Leu Phe Leu Ile Leu Ala Asp Met Val Gly Ile Pro Cys Lys Leu Val
            260                 265                 270

Lys Gly Ser His Tyr Thr Gly Val Val Asp Asp Ala Ile Asn Ile Ile
        275                 280                 285

Lys Met Asp Asn Lys Arg Glu Phe Leu Val Asp Val Met Ala Ala Pro
    290                 295                 300

Gly Thr Leu Ile Pro Ala Asp Val Phe Asn Ser Lys Gly Thr Pro Phe
305                 310                 315                 320

Asn Phe Ser Gln Thr Leu Gly Gln Asn Gln Val Val Glu Ser Ala Ser
                325                 330                 335

Asn Ile Glu Asp Asp Pro Val Ala Leu Gln Ser Glu His Glu His Tyr
            340                 345                 350

Gln Gly His Met Phe Ala Asn Asn Asp Arg Val Ser Asp Asn Leu Ser
        355                 360                 365

Ser Tyr Glu Asn Thr Met Thr Ala Gly Ser Ser Ala Ser Glu Pro Gly
    370                 375                 380

Thr Leu Gly Lys Ala Ser Thr Leu Ala Gly Ala Pro Ser Lys Gln Lys
385                 390                 395                 400

Lys Asn Leu Gln Leu Ile Pro Asp Ser His Glu Ile Asp Glu Ser Arg
                405                 410                 415

Asn Leu Phe Ala Glu Phe Asp Pro Phe Asn Ala Thr Glu Ser Gly Lys
            420                 425                 430

Ser Ser Leu Ala Phe Lys Gly Leu Asn Asn Arg Asn Ser Asp Phe Arg
        435                 440                 445

Arg Arg Arg Glu Asn Val Val Pro Pro Ser Ala Arg Ser Gln Gln Pro
    450                 455                 460

Leu Val Xaa Lys Asn Trp Ser Ala Cys Asn Asp Ile Ser Asn Asn Lys
465                 470                 475                 480

Gln Tyr Asn Val Ala Asp Gly Ser Val Pro Arg Arg Asn Ala Thr Asp
                485                 490                 495

Asn Ala Ser Ser Ser Gln Leu Ala Leu Ser Thr Ala Lys His Tyr Asn
            500                 505                 510

Pro Asn Val Arg Glu Leu Asn Asp Arg Met Tyr Ala Ala Pro Ala Arg
        515                 520                 525

Asn Tyr Asp Asn Arg Ile Ile Gly Thr Ser Ala Met Ala Lys Ala Ser
    530                 535                 540
```

```
Thr Gly Asp Cys Leu Asp Arg Ser Gln Val Pro Pro Gly Leu Tyr Tyr
545                 550                 555                 560

Asp Lys Met Leu Gly Thr Ser Ser Met Asn Thr Ala Ser Ser Ser Gly
                565                 570                 575

Ile Gly Lys Val Ala Glu Lys Asp Leu Gln Asn Asp Leu Glu Lys Gly
                580                 585                 590

Pro Ile Tyr Ser Arg Phe Asp Gly Glu Leu Ser Lys Asn Ala Gln Gly
            595                 600                 605

Phe Thr Pro Glu Arg Asp Glu His Lys Glu Asn Cys Gly Ser Tyr Asp
        610                 615                 620

His Arg Met Leu His Pro Asp Pro Arg Lys Ser Pro Leu Asp Arg Phe
625                 630                 635                 640

Met Asp Arg Pro Arg Gln Asn Ile Glu Cys Val Ser Pro Ser Gln Val
                645                 650                 655

Gly Ser Ser Lys Val Asp Leu Val Leu Asp Glu Val Ser Glu Cys Glu
                660                 665                 670

Ile Leu Trp Glu Asp Leu Val Ile Asp Glu Arg Ile Gly Ile Gly Ser
            675                 680                 685

Tyr Gly Glu Val Tyr His Ala Asp Trp Asn Gly Thr Glu Val Ala Val
        690                 695                 700

Lys Lys Phe Leu Asp Gln Glu Phe Tyr Gly Asp Ala Leu Glu Glu Phe
705                 710                 715                 720

Arg Cys Glu Val Arg Ile Met Arg Arg Leu Arg His Pro Asn Ile Val
                725                 730                 735

Leu Phe Met Gly Ala Val Thr Arg Pro Pro His Leu Ser Ile Val Ser
                740                 745                 750

Glu Tyr Leu Pro Arg Gly Ser Leu Tyr Lys Ile Ile His Arg Pro Asn
            755                 760                 765

Cys Gln Ile Asp Glu Lys Arg Ile Lys Met Ala Leu Asp Val Ala
        770                 775                 780

Arg Gly Met Asn Cys Leu His Thr Ser Val Pro Thr Ile Val His Arg
785                 790                 795                 800

Asp Leu Lys Ser Pro Asn Leu Leu Val Asp Asp Asn Trp Thr Val Lys
                805                 810                 815

Val Cys Asp Phe Gly Leu Ser Arg Leu Lys His Ser Thr Phe Leu Ser
                820                 825                 830

Ser Lys Ser Thr Ala Gly Thr Pro Glu Trp Met Ala Pro Glu Val Leu
        835                 840                 845

Arg Asn Glu Gln Ser Asn Glu Lys Cys Asp Ile Tyr Ser Phe Gly Val
850                 855                 860

Ile Leu Trp Glu Leu Ala Thr Leu Arg Lys Pro Trp His Gly Met Asn
865                 870                 875                 880

Gln Met Gln Val Val Gly Ala Val Gly Phe Gln Asp Arg Arg Leu Asp
                885                 890                 895

Ile Pro Lys Glu Val Asp Pro Ile Val Ala Ser Ile Ile Arg Asp Cys
            900                 905                 910

Trp Gln Lys Asp Pro Asn Leu Arg Pro Ser Phe Ile Gln Leu Thr Ser
        915                 920                 925

Tyr Leu Lys Thr Leu Gln Arg Leu Val Ile Pro Ser His Gln Glu Thr
930                 935                 940
```

-continued

```
Ala Ser Asn His Val Pro Tyr Glu Ile Ser Leu Tyr Arg Thr Ala His
945                 950                 955                 960

Leu Thr Ser Leu Pro Arg Gly Cys His Pro
                965                 970
```